(12) United States Patent
Chin et al.

(10) Patent No.: US 8,834,508 B2
(45) Date of Patent: Sep. 16, 2014

(54) METHODS, TOOLS AND DEVICES FOR PERCUTANEOUS ACCESS IN MINIMALLY INVASIVE SPINAL SURGERIES

(75) Inventors: Kingsley R. Chin, Wilton Manors, FL (US); Craig Henshaw, Charlestown, MA (US); Matthew Ibarra, Lakewood, CA (US); Vito Lore, Somerville, MA (US); Jeremy Crossgrove, Storrs, CT (US)

(73) Assignee: Spinefrontier Inc, Beverly, MA (US)

( * ) Notice: Subject to any disclaimer, the term of this patent is extended or adjusted under 35 U.S.C. 154(b) by 6 days.

(21) Appl. No.: 13/480,691

(22) Filed: May 25, 2012

(65) Prior Publication Data

US 2012/0303039 A1 Nov. 29, 2012

Related U.S. Application Data

(60) Provisional application No. 61/490,655, filed on May 27, 2011.

(51) Int. Cl.
```
A61M 29/00        (2006.01)
A61B 17/70        (2006.01)
A61B 17/34        (2006.01)
A61B 17/16        (2006.01)
A61B 17/02        (2006.01)
A61B 17/00        (2006.01)
```

(52) U.S. Cl.
CPC ........ *A61M 29/00* (2013.01); *A61B 2017/0256* (2013.01); *A61B 17/70* (2013.01); *A61B 17/3421* (2013.01); *A61B 2017/0262* (2013.01); *A61B 17/0206* (2013.01); *A61B 17/7092* (2013.01); *A61B 17/025* (2013.01); *A61B 17/7077* (2013.01); *A61B 17/1671* (2013.01); *A61B 2017/0046* (2013.01); *A61B 17/1626* (2013.01)
USPC .......................... 606/191; 606/108; 604/104

(58) Field of Classification Search
USPC ................... 606/96, 99, 104, 86 A, 191, 108; 623/17.11–17.16; 604/104
See application file for complete search history.

(56) References Cited

U.S. PATENT DOCUMENTS

| | | | |
|---|---|---|---|
| 4,449,532 A * | 5/1984 | Storz | 606/191 |
| 5,059,194 A | 10/1991 | Michelson | |
| 5,928,139 A | 7/1999 | Koros et al. | |
| 6,224,603 B1 | 5/2001 | Marino | |
| 6,270,498 B1 | 8/2001 | Michelson | |

(Continued)

FOREIGN PATENT DOCUMENTS

| | | |
|---|---|---|
| EP | 1113756 | 8/2000 |
| WO | WO0048521 A1 | 8/2000 |

(Continued)

*Primary Examiner* — Pedro Philogene
*Assistant Examiner* — Christina Negrellirodrigue
(74) *Attorney, Agent, or Firm* — AKC Patents LLC; Aliki K. Collins

(57) ABSTRACT

A cannula assembly for providing percutaneous access in minimally invasive spinal surgeries, includes an outer cannula, a nerve probe dilator and a multistage dilator system comprising a first dilator, a second dilator, a third dilator and a fourth dilator. The outer cannula and the dilators are slidable relative to each other and are arranged sequentially so that the fourth dilator surrounds the nerve probe dilator, the third dilator slides over a surface of the fourth dilator, the second dilator slides over a surface of the third dilator, the first dilator slides over a surface of the second dilator, and the outer cannula surrounds the first dilator.

19 Claims, 40 Drawing Sheets

(56) References Cited

U.S. PATENT DOCUMENTS

| | | |
|---|---|---|
| 6,648,891 B2 | 11/2003 | Kim |
| 6,916,330 B2 | 7/2005 | Simonson |
| 7,008,431 B2 | 3/2006 | Simonson |
| 7,033,362 B2 | 4/2006 | McGahan et al. |
| 7,033,392 B2 | 4/2006 | Schmiel et al. |
| 7,491,205 B1 | 2/2009 | Michelson |
| 7,494,463 B2 | 2/2009 | Nehls |
| 7,594,888 B2 * | 9/2009 | Raymond et al. ............. 600/219 |
| 7,618,431 B2 | 11/2009 | Roehm, III et al. |
| 7,625,381 B2 | 12/2009 | Michelson |
| 7,736,369 B2 | 6/2010 | Arnin et al. |
| 7,811,303 B2 | 10/2010 | Fallin et al. |
| 7,914,530 B2 | 3/2011 | Michelson |
| 2002/0077641 A1 | 6/2002 | Michelson |
| 2002/0198533 A1 | 12/2002 | Geisler et al. |
| 2003/0032962 A1 * | 2/2003 | McGahan et al. ............. 606/80 |
| 2003/0083688 A1 * | 5/2003 | Simonson ..................... 606/191 |
| 2003/0195405 A1 | 10/2003 | Marino et al. |
| 2004/0059339 A1 | 3/2004 | Roehm, III et al. |
| 2005/0004593 A1 | 1/2005 | Simonson |
| 2005/0080443 A1 * | 4/2005 | Fallin et al. ................... 606/191 |
| 2005/0216002 A1 | 9/2005 | Simonson |
| 2006/0004398 A1 | 1/2006 | Binder, Jr. et al. |
| 2006/0030872 A1 | 2/2006 | Culbert et al. |
| 2006/0084844 A1 | 4/2006 | Nehls |
| 2006/0195109 A1 | 8/2006 | McGahan et al. |
| 2006/0217754 A1 | 9/2006 | Boehm, III et al. |
| 2006/0241626 A1 | 10/2006 | McGahan et al. |
| 2006/0247649 A1 | 11/2006 | Rezach et al. |
| 2006/0247651 A1 | 11/2006 | Roehm, III et al. |
| 2007/0191856 A1 | 8/2007 | Gil et al. |
| 2008/0051821 A1 | 2/2008 | Gephart |
| 2008/0177270 A1 | 7/2008 | Sorrenti et al. |
| 2008/0262494 A1 | 10/2008 | Moore et al. |
| 2008/0287981 A1 * | 11/2008 | Culbert et al. ................ 606/191 |
| 2008/0294171 A1 * | 11/2008 | Boehm et al. .................. 606/90 |
| 2009/0076516 A1 | 3/2009 | Lowry et al. |
| 2009/0149857 A1 | 6/2009 | Culbert et al. |
| 2010/0114147 A1 | 5/2010 | Biyani |
| 2010/0222824 A1 | 9/2010 | Simonson |
| 2010/0331849 A1 | 12/2010 | Riesinger et al. |
| 2011/0009869 A1 | 1/2011 | Marino et al. |
| 2012/0010471 A1 | 1/2012 | Mire et al. |

FOREIGN PATENT DOCUMENTS

| | | |
|---|---|---|
| WO | WO2006044932 A2 | 4/2006 |
| WO | WO2008048450 A3 | 4/2008 |
| WO | WO2009036360 A1 | 3/2009 |

* cited by examiner

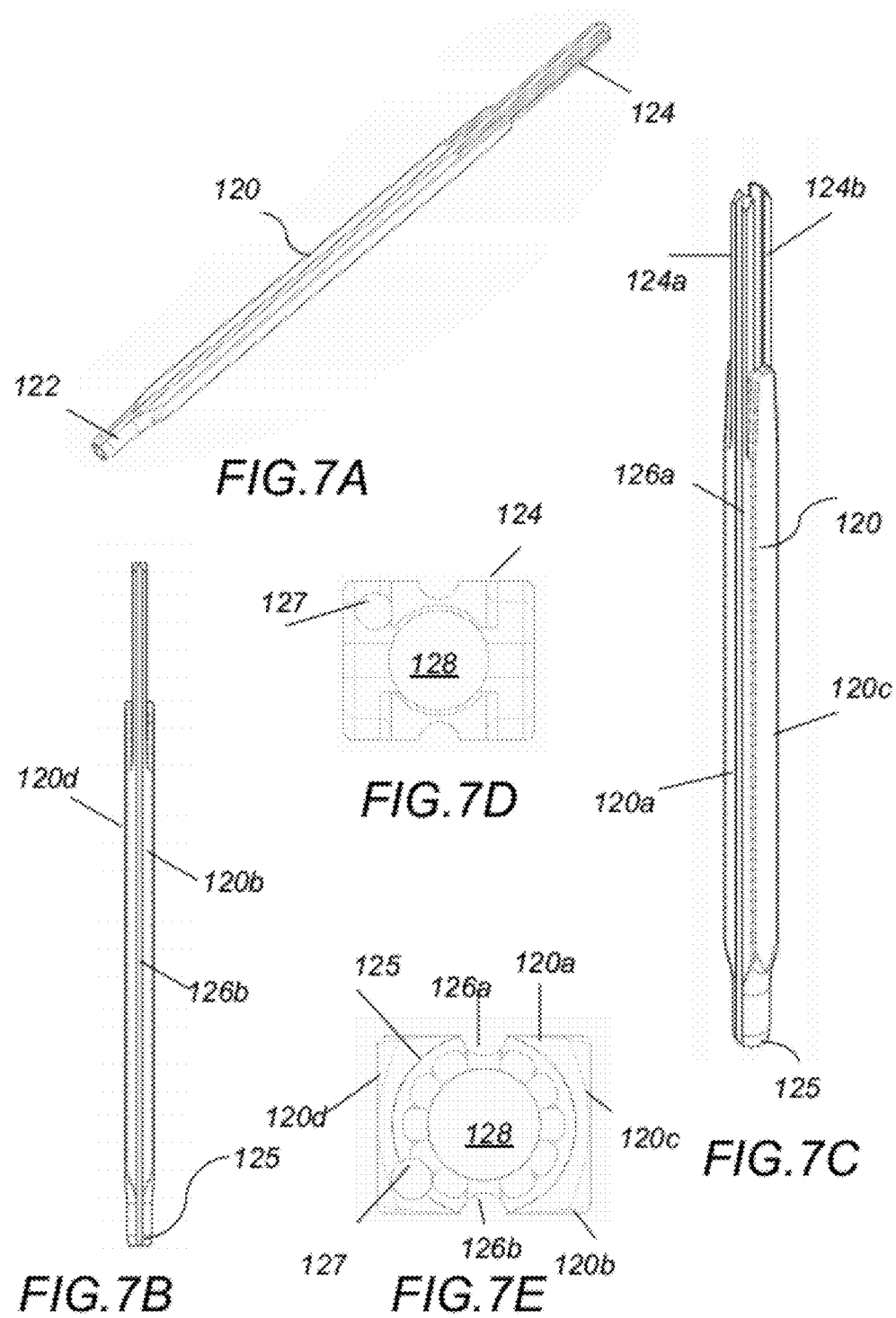

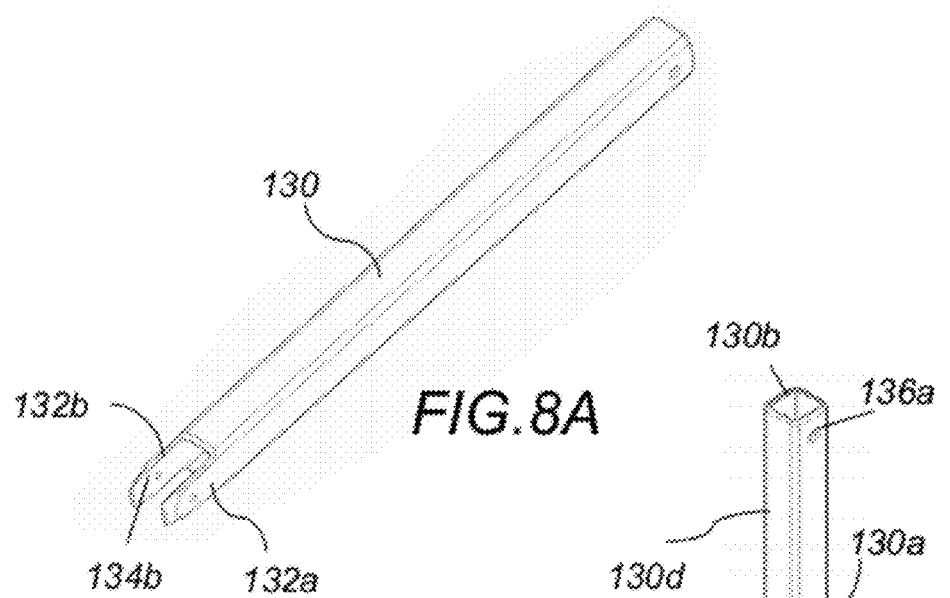
FIG.8A
FIG.8C
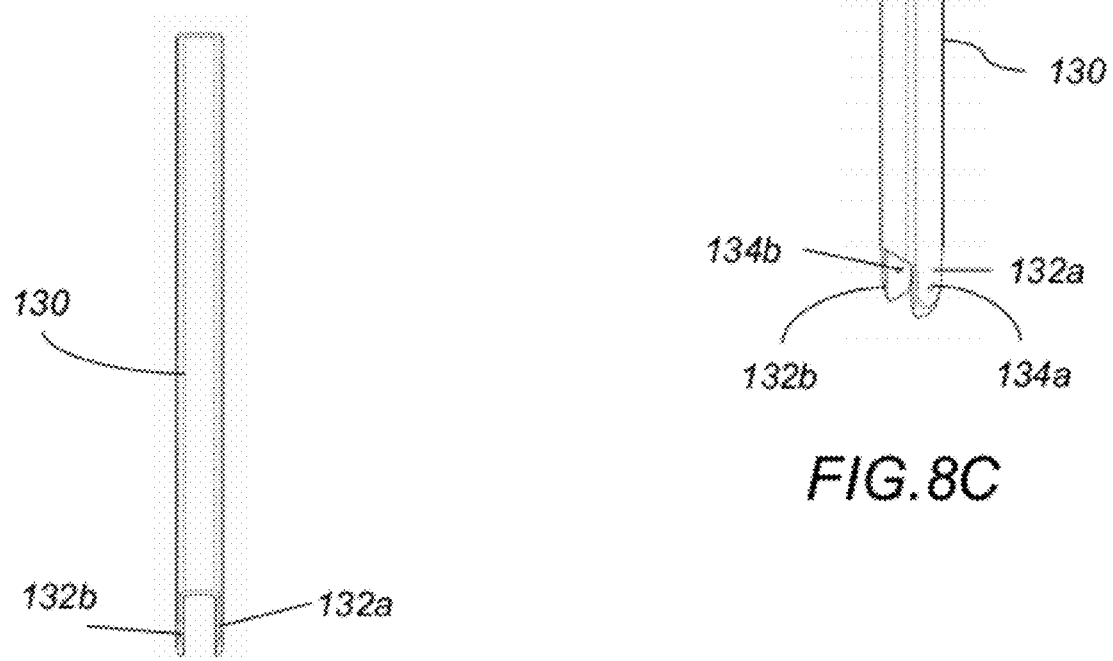
FIG.8B

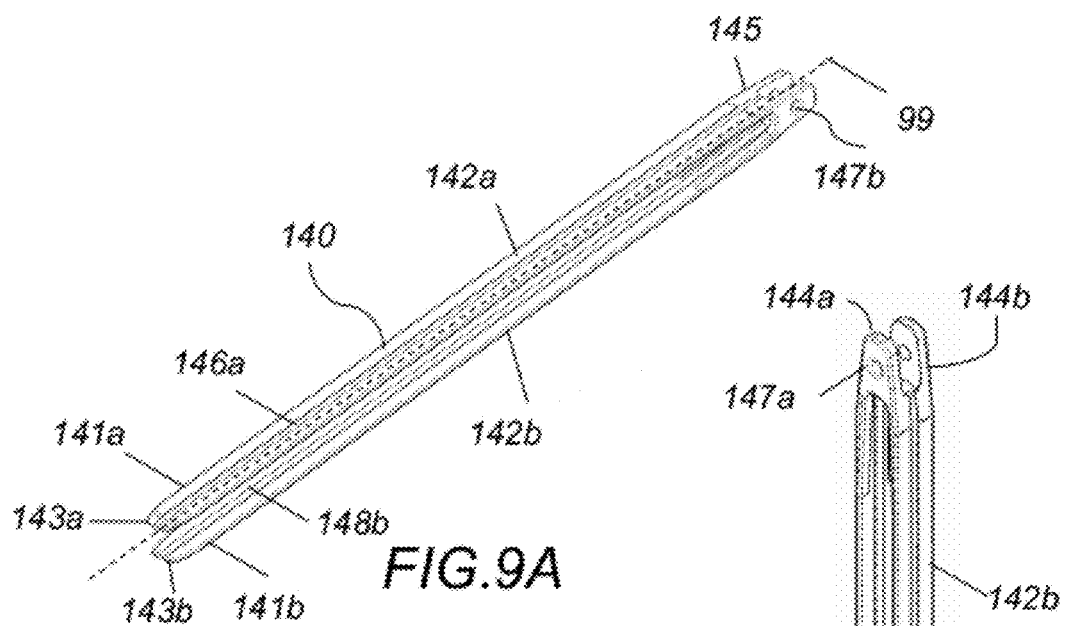
FIG.9A
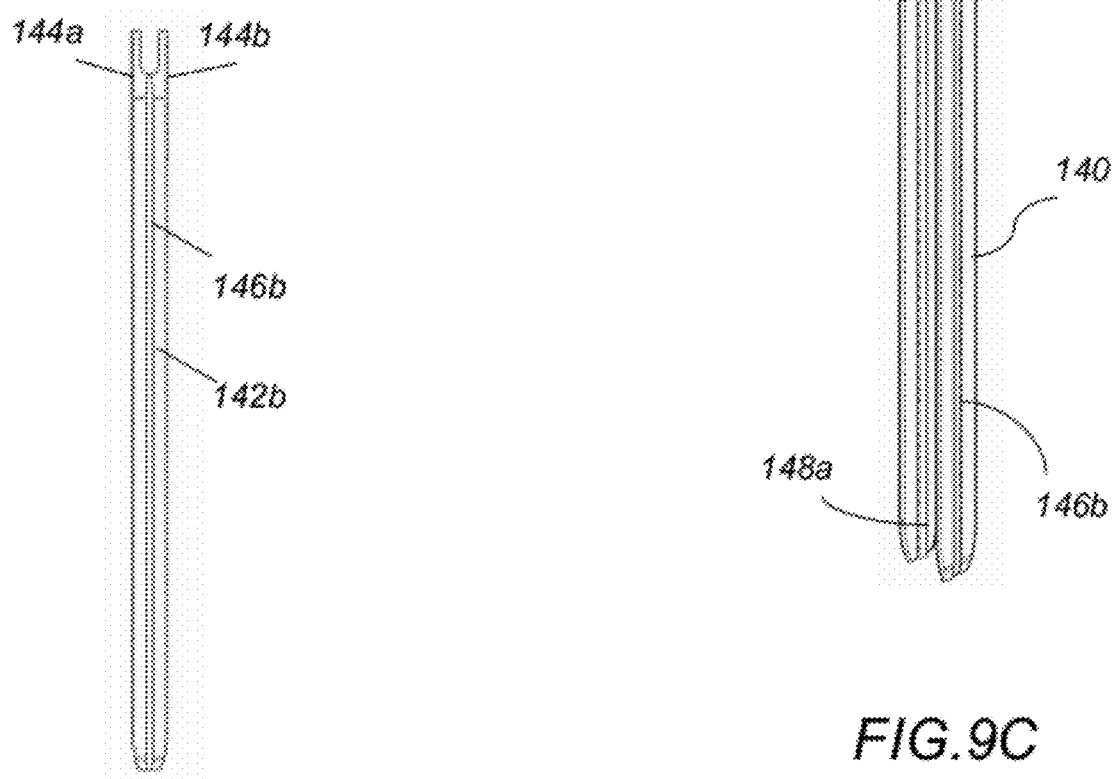
FIG.9B
FIG.9C

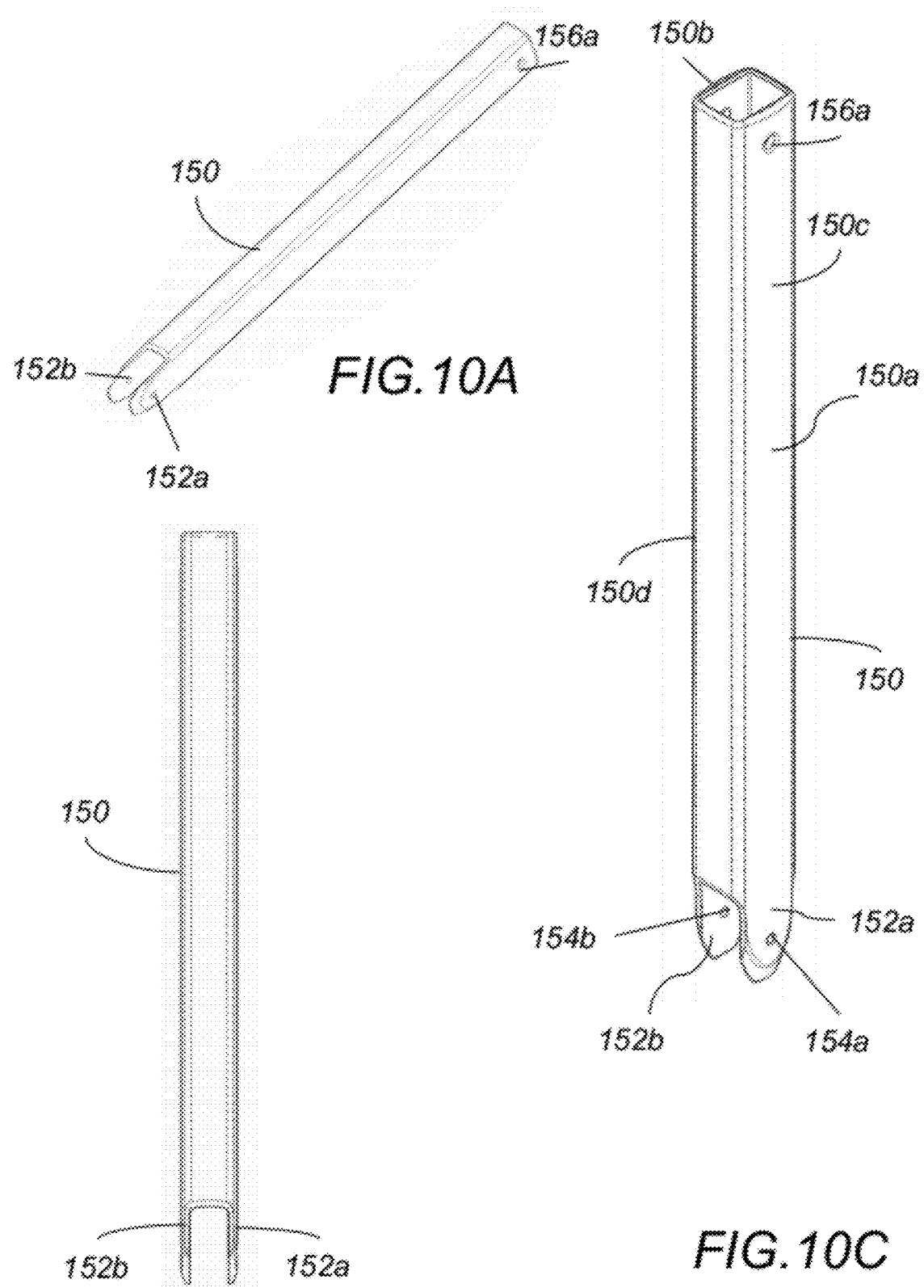

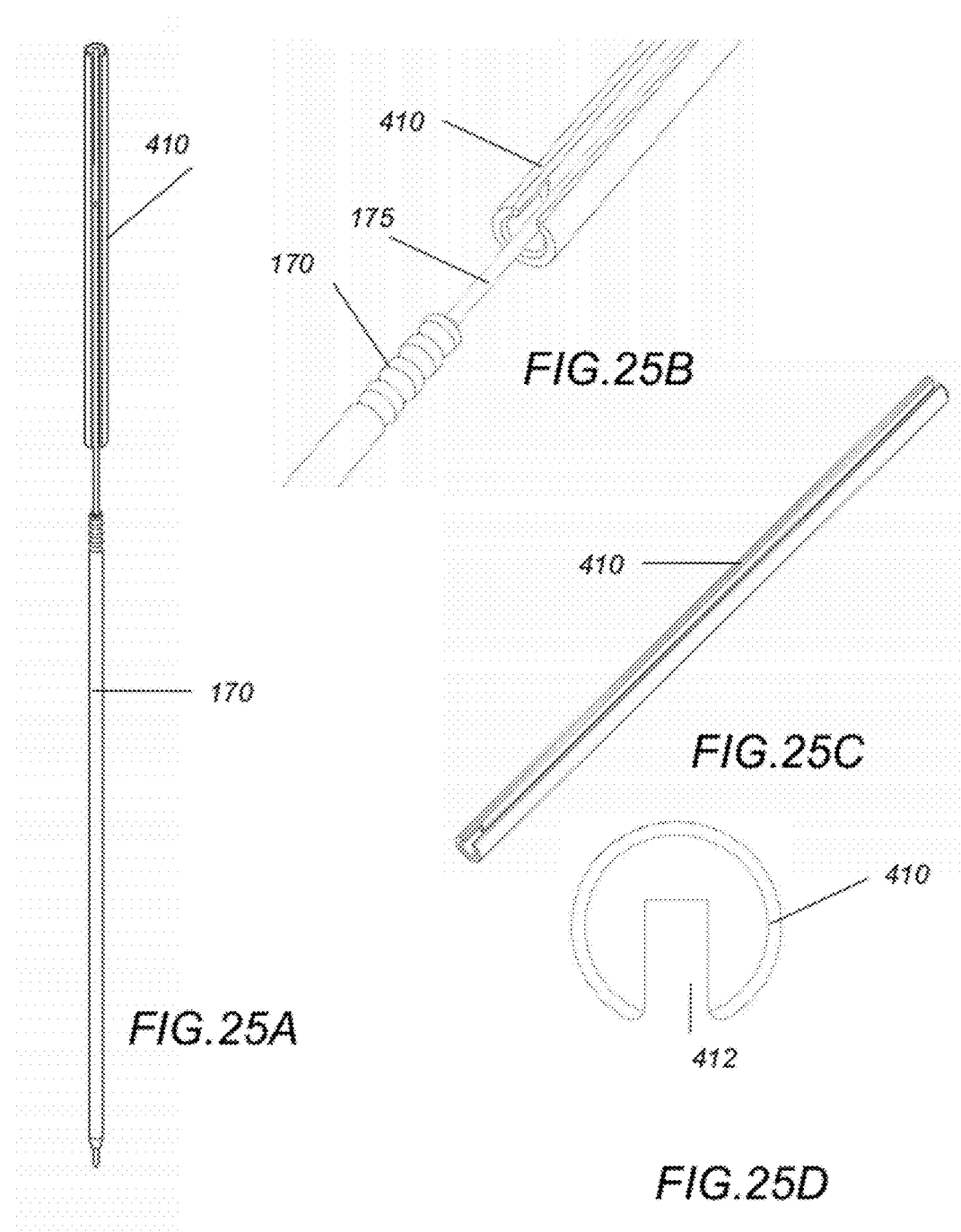

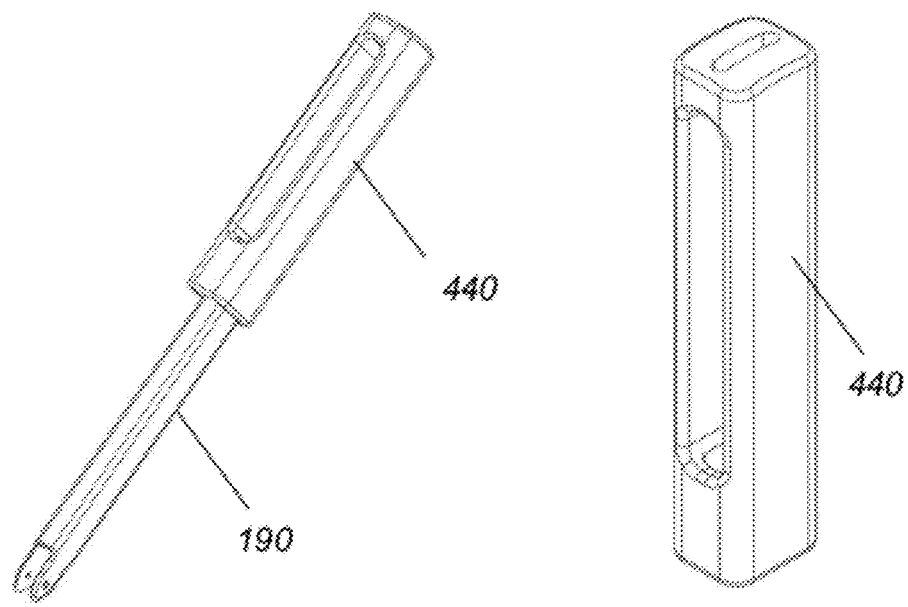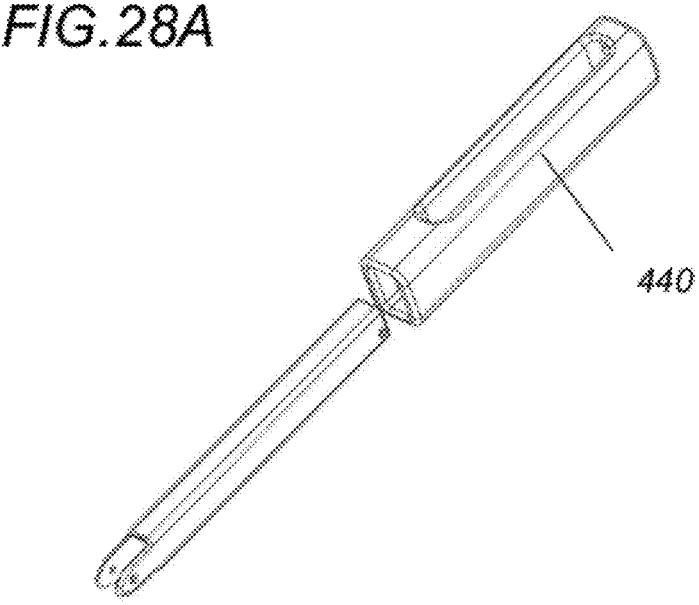
FIG.28A
FIG.28C
FIG.28B

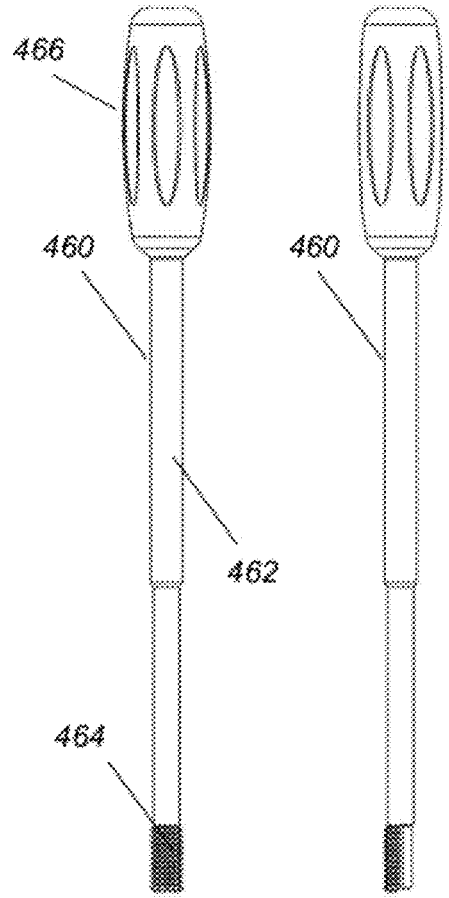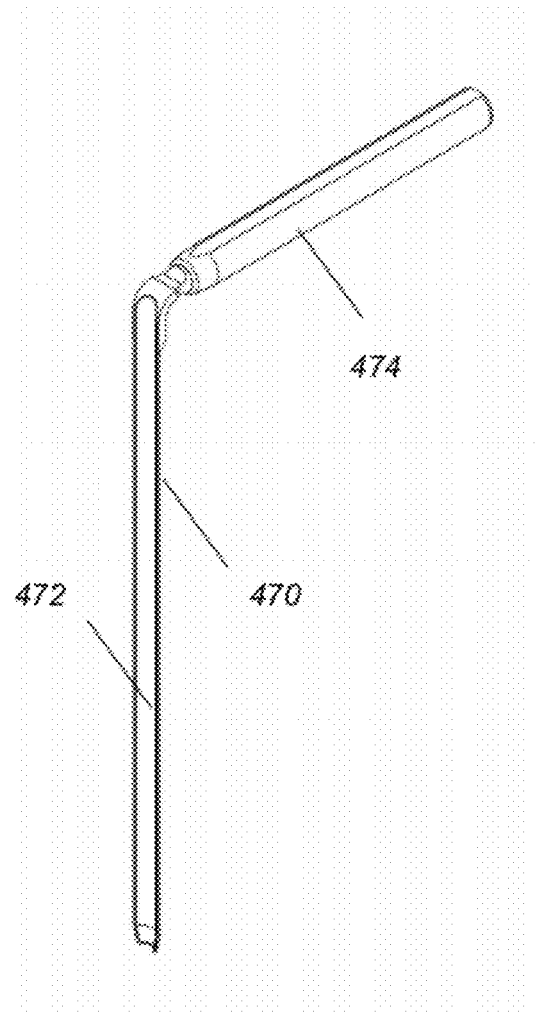
FIG.33A  FIG.33B  FIG.34

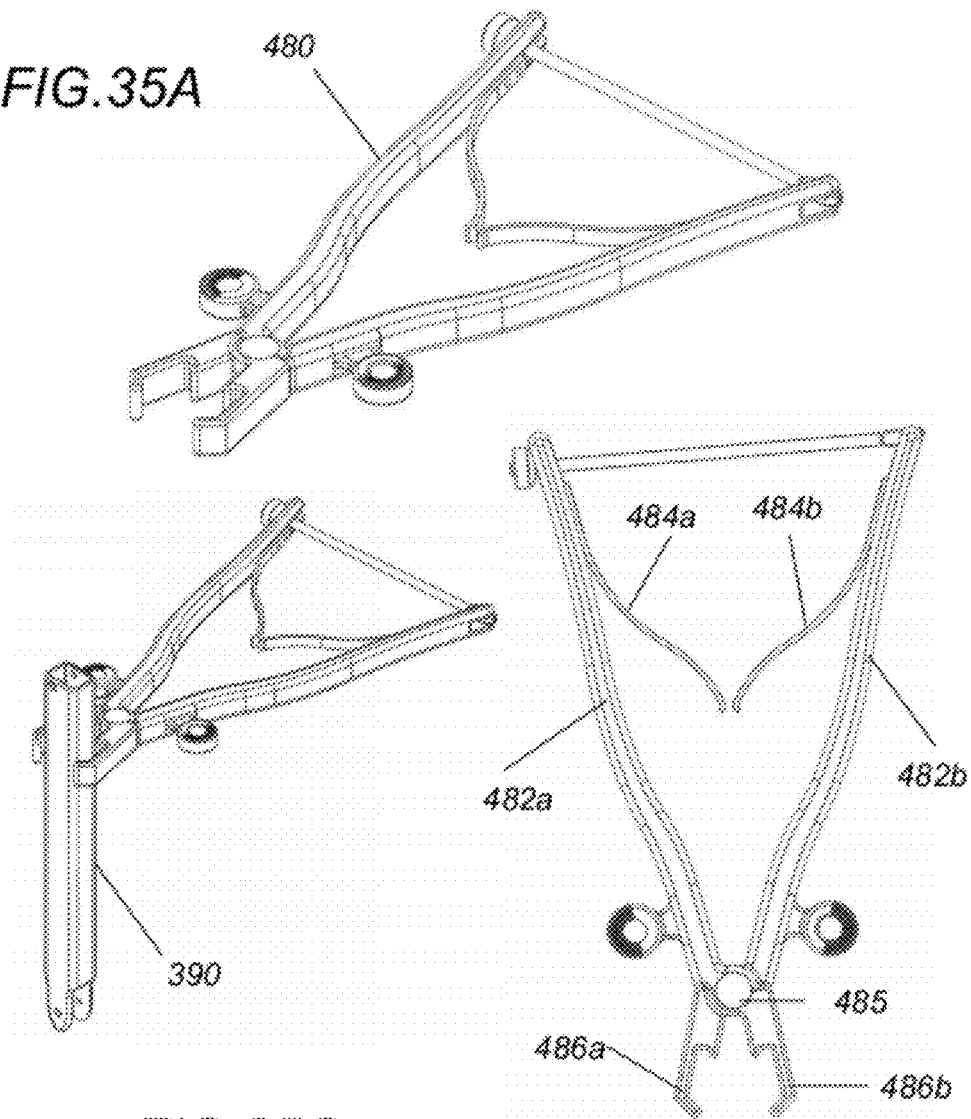

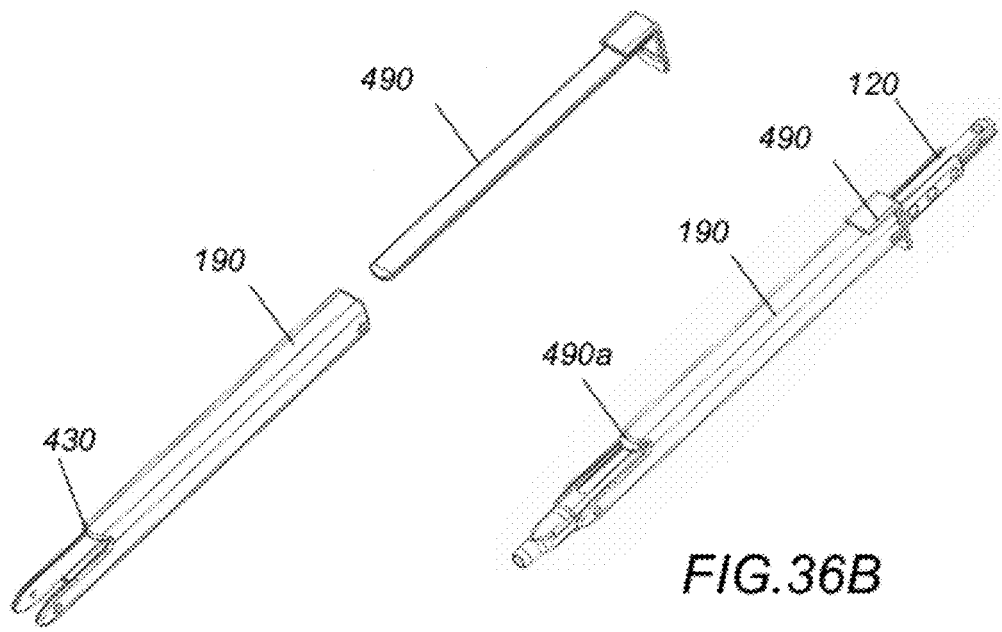
FIG.36A
FIG.36B
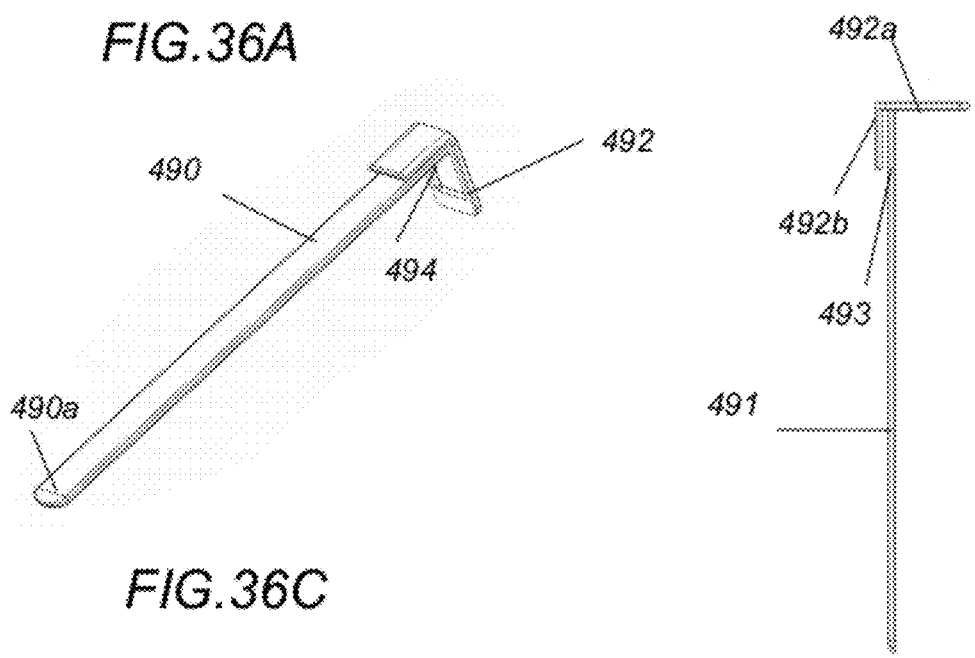
FIG.36C
FIG.36D

METHODS, TOOLS AND DEVICES FOR PERCUTANEOUS ACCESS IN MINIMALLY INVASIVE SPINAL SURGERIES

CROSS REFERENCE TO RELATED CO-PENDING APPLICATIONS

This application claims the benefit of U.S. provisional application Ser. No. 61/490,655 filed May 27, 2011 and entitled "IMPROVED METHODS, TOOLS AND DEVICES FOR PERCUTANEOUS ACCESS IN MINIMALLY INVASIVE SPINAL SURGERIES", the contents of which are expressly incorporated herein by reference.

FIELD OF THE INVENTION

The present invention relates to improved methods, tools and devices for providing percutaneous access in minimally invasive spinal surgeries, and more particularly to an access cannula that includes multi-stage dilators and multi-stage cannulae.

BACKGROUND OF THE INVENTION

It is well known that traditional surgical procedures in locations deep within a patient's body require a long incision, extensive muscle stripping, prolonged retraction of muscles for visualization, and denervation and devascularization of the adjacent tissue. These procedures result in extensive tissue traumatization and consequently in prolonged recovery time, risk of infections, high hospitalization costs, pain that can be more severe than the pain due to the initial ailment, and in some cases permanent scarring. In minimally invasive surgical procedures, portals are used to access the locations deep in the patient's body. The use of portals rather than a long incision causes less trauma to the adjacent tissue, reduces the recovery time and pain and may be performed in some case under only local anesthesia. The avoidance of general anesthesia reduces post-operative recovery time and the risk of complications.

Minimally invasive surgical procedures are especially desirable for spine surgeries because spine pathologies are located deep within the body without clear muscle planes and there is danger of damaging the adjacent neural and vascular tissues. In treating the majority of spinal pathologies, the spinal muscles are stripped from the bony elements of the spine followed by laminectomy to expose the dura, the nerve roots, and the discs. The incision has to be wide enough and the tissues have to be retracted to maintain a channel from the skin to the floor of the spinal canal that will allow direct visualization. The destruction to the spinal structures is even more extensive during fusion procedures, which require more lateral tissue dissection and exposure to access the transverse processes and pedicles for placement of pedicle screws, rod constructs for stability, and bone graft under direct vision.

Multiple attempts have been made to improve the techniques, devices, and instrumentations used for minimal and percutaneous surgery. These include use of percutaneous needle administration of chemonucleolytic agents to enzymatically dissolve the disc and the use of microscopes and loupe magnification to limit the incision size. These two approaches are at the foundation of minimal access surgery, one using an injectable agent and the other using a device to limit the exposure while maximizing the visualization. Unfortunately, the effectiveness and safety of the enzyme, chymopapain used for chemonucleolysis, have been complicated by severe spasms, post-operative pain, and sensitivity reactions including anaphylactic shock. Loupe magnification and microscopes are helpful for improving visualization but are not effective without retractor systems and specialized instruments and devices to make minimal access surgery effective.

Substantial progress has been made to develop the necessary devices, instruments, and methods to effectively improve minimal access surgery resulting in improved visualization, less tissue injury, less general anesthesia exposure and improved recovery time and post-operative pain. For example U.S. Pat. Nos. 5,792,044 and 5,902,231 by Foley et al., demonstrate some of the improved methods and instruments for percutaneous surgeries.

A problem that occurs frequently in minimally invasive surgical procedures is related to the fact that it is not always known how deep the pathology is located. Accordingly there is a need for a portal with a variable length to accommodate the locations of the various pathologies. Furthermore, in spine fusion procedures intervertebral spacers or connecting elements, such as rods, plates or wires are placed and fixed between two or more locations of the spine. Placement of these spacers or connecting elements requires open surgery, which is currently one of the major limitations of other percutaneous cannula access methodologies. Accordingly there is a need for improved methods, tools and devices that provide percutaneous access in minimally invasive spinal surgeries.

SUMMARY OF THE INVENTION

The present invention relates to methods and devices for improving percutaneous access in minimally invasive surgeries, and more particularly to methods and devices that provide access channels to locations deep within a patient's body at various angles and directions and to an access cannula that includes multi-stage dilators and multi-stage cannulae.

In general, in one aspect, the invention features a cannula assembly for providing percutaneous access in minimally invasive spinal surgeries, including an outer cannula, a nerve probe dilator and a multistage dilator system comprising a first dilator, a second dilator, a third dilator and a fourth dilator. The outer cannula and the dilators are slidable relative to each other and are arranged sequentially so that the fourth dilator surrounds the nerve probe dilator, the third dilator slides over a surface of the fourth dilator, the second dilator slides over a surface of the third dilator, the first dilator slides over a surface of the second dilator, and the outer cannula surrounds the first dilator.

Implementations of this aspect of the invention may include one or more of the following features. The outer cannula comprises an elongated tube having first and second opposite sides, third and fourth opposite sides and a rectangular cross section. The first and second opposite sides comprise distal ends terminating in two parallel fork extensions, respectively. The parallel fork extensions are tapered and terminate into inverted trapezoids. The parallel fork extensions are rigid and are dimensioned to fit within an intervertebral space. The distal end of the third side is shorter than the distal end of the fourth side. Each of the first, second, and third dilators comprises a single elongated blade terminating into a tapered distal end and having a proximal end comprising two parallel extensions and a groove formed between the two parallel extensions. Each of the first, second, and third dilators comprises an inner surface having tongue protrusions and each of the second and third and fourth dilators comprises an outer surface having an elongated groove. The tongue protrusions of the first dilator are configured to slide and engage the elongated groove of the second dilator, the tongue protrusions of the second dilator are configured to slide and engage the elongated groove of the third dilator, and the tongue protrusions of the third dilator are configured to slide and engage the elongated groove of the fourth dilator. The fourth dilator comprises a cylindrical inner lumen, rectangular outer surfaces, a cylindrical distal end with a serrated edge and a proximal end having two elongated parallel extensions separated by a distance equal to the diameter of the cylindrical inner lumen. Each of the third and fourth dilators comprises two parallel blades extending from a common proximal end and having separated distal ends terminating in inverted trapezoids. The nerve probe dilator comprises a cylindrical main shaft having a conical shaped distal end and a cylindrical lumen extending the entire length of the cylindrical main shaft and being dimensioned to receive a nerve probe. The nerve probe dilator further comprises a trephine drill surrounding the conical distal end. The cylindrical main shaft comprises a plurality of through openings extending perpendicular to the cylindrical lumen. The assembly may further include a nerve probe impactor comprising an elongated cylindrical body having an elongated slot extending along the length of the cylindrical body. The assembly may further include an impaction handle comprising a rectangular cross section and being dimensioned to slide over the outer cannula. The assembly may further include a multipurpose tool comprising a rectangular body having openings shaped and dimensioned to slide over the nerve probe dilator, the dilators and the outer cannula. The assembly may further include a pedicle reamer tool. The assembly may further include a nerve shield tool. The assembly may further include a cannula holder tool. The cannula holder comprises two pivotally connected spring loaded handles and the two handles comprise proximal ends configured to compress two inner springs, respectively, and distal ends having inner surfaces shaped and dimensioned to match the outer shape and dimensions of the outer cannula.

In general, in another aspect, the invention features a cannula assembly for providing percutaneous access in minimally invasive spinal surgeries, including a multistage cannula system, a multistage dilator system and a nerve probe dilator. The multistage cannula system includes a first cannula, a second cannula, a third cannula and a fourth cannula. The multistage dilator system includes a first dilator, a second dilator, a third dilator and a fourth dilator. The cannulae and the dilators are slidable relative to each other and are arranged sequentially so that the fourth dilator surrounds the nerve probe dilator, the fourth cannula surrounds the fourth dilator, the third dilator slides over a surface of the fourth cannula, the third cannula surrounds the third dilator, the second dilator slides over a surface of the third cannula, the second cannula surrounds the second dilator, the first dilator slides over a surface of the second cannula, and the first cannula surrounds the first dilator.

In general, in another aspect, the invention features a method for providing percutaneous access in minimally invasive spinal surgeries for inserting a spinal implant, including the following steps. First, providing a cannula assembly comprising an outer cannula, a nerve probe dilator and a multistage dilator system comprising a first dilator, a second dilator, a third dilator and a fourth dilator. The outer cannula and the dilators are slidable relative to each other and are arranged sequentially so that the fourth dilator surrounds the nerve probe dilator, the third dilator slides over a surface of the fourth dilator, the second dilator slides over a surface of the third dilator, the first dilator slides over a surface of the second dilator, and the outer cannula surrounds the first dilator. Next, inserting a nerve probe into the nerve probe dilator and impacting the nerve probe dilator into a first spinal location under the guidance of the nerve probe. Next, sliding the fourth dilator over the nerve probe dilator and impacting the fourth dilator into the first spinal location thereby forming an opening in the first spinal location. Next, measuring the opening's dimensions and if the spinal implant's dimensions are smaller than the opening's dimensions sliding the outer cannula over the fourth dilator and impacting the outer cannula into the first spinal location, and then removing the dilators and inserting the spinal implant into the opening. If the spinal implant's dimensions are larger that the opening's dimensions, the method further includes sequentially impacting the third, second and first dilators into the first spinal location until the spinal implant's dimensions are smaller than the opening's dimensions.

The details of one or more embodiments of the invention are set forth in the accompanying drawings and description below. Other features, objects, and advantages of the invention will be apparent from the following description of the preferred embodiments, the drawings, and the claims

BRIEF DESCRIPTION OF THE DRAWINGS

Referring to the figures, wherein like numerals represent like parts throughout the several views:

FIG. 7A is a perspective view of an 8 mm dilator of the multi-component cannula system of FIG. 5A;

FIG. 7B is a front view of the 8 mm dilator of FIG. 7A;

FIG. 7C is a front isometric view of the 8 mm dilator of FIG. 7A;

FIG. 7D is a top isometric view of the 8 mm dilator of FIG. 7A;

FIG. 7E is a bottom isometric view of the 8 mm dilator of FIG. 7A;

FIG. 8A is a perspective view of a 10 mm cannula of the multi-component cannula system of FIG. 5A;

FIG. 8B is a front view of the 10 mm cannula of FIG. 8A;

FIG. 8C is a front isometric view of the 10 mm cannula of FIG. 8A;

FIG. 9A is a perspective view of a 10 mm dilator of the multi-component cannula system of FIG. 5A;

FIG. 9B is a front view of the 10 mm dilator of FIG. 9A;

FIG. 9C is a front isometric view of the 10 mm dilator of FIG. 9A;

FIG. 10A is a perspective view of a 12 mm cannula of the multi-component cannula system of FIG. 5A;

FIG. 10B is a front view of the 12 mm cannula of FIG. 10A;

FIG. 10C is a front isometric view of the 12 mm cannula of FIG. 10A;

FIG. 25A depicts the nerve probe impactor inserted over the nerve probe dilator;

FIG. 25B depicts a detailed view of the nerve probe impactor inserted over the nerve probe dilator;

FIG. 25C depicts a perspective view of the nerve probe impactor;

FIG. 25D depicts a top view of the nerve probe impactor;

FIG. 28A depicts a cannula impactor inserted over a cannula;

FIG. 28B depicts the cannula impactor of FIG. 28A prior to being inserted over a cannula:

FIG. 28C depicts a perspective view of the cannula impactor of FIG. 28A;

FIG. 33A depicts a front view of a pedicle reamer tool;

FIG. 33B depicts a side view of the pedicle reamer tool of FIG. 33A;

FIG. 34 depicts a nerve shield tool;

FIG. 35A depicts a cannula holder tool;

FIG. 35B is a top view of the cannula holder tool of FIG. 35A;

FIG. 35C depicts the cannula holder tool of FIG. 35A holding a cannula;

FIG. 36A depicts a tissue shim dilator near a cannula;

FIG. 36B depicts the tissue shim dilator of FIG. 36A inserted into the cannula;

FIG. 36C depicts a front perspective view of the tissue shim dilator of FIG. 36A; and FIG. 36D depicts a side view of the tissue shim dilator of FIG. 36A.

DETAILED DESCRIPTION OF THE INVENTION

The present invention relates to improved methods, tools and devices for providing percutaneous access in minimally invasive spinal surgeries, and more particularly to cannula system that includes multi-stage dilators and multi-stage cannulae.

Figure 1A:
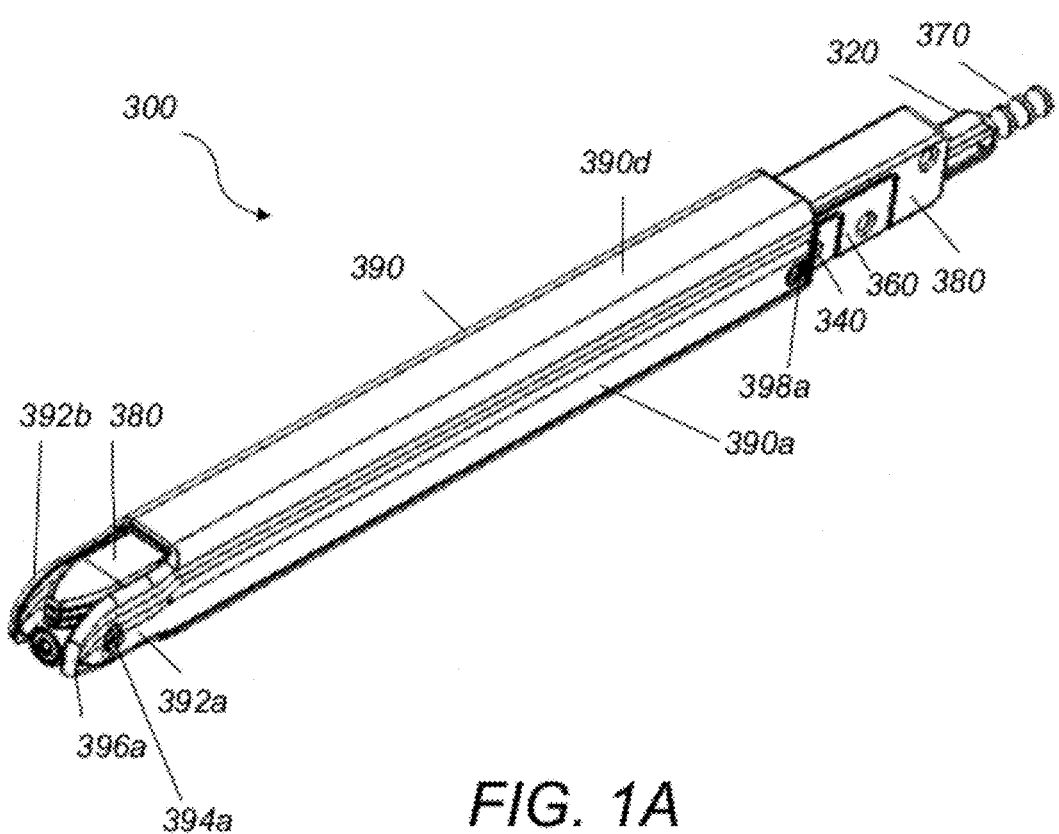
FIG. 1A is a front perspective view of a first embodiment of a multi-component cannula system.
Figure 1B:
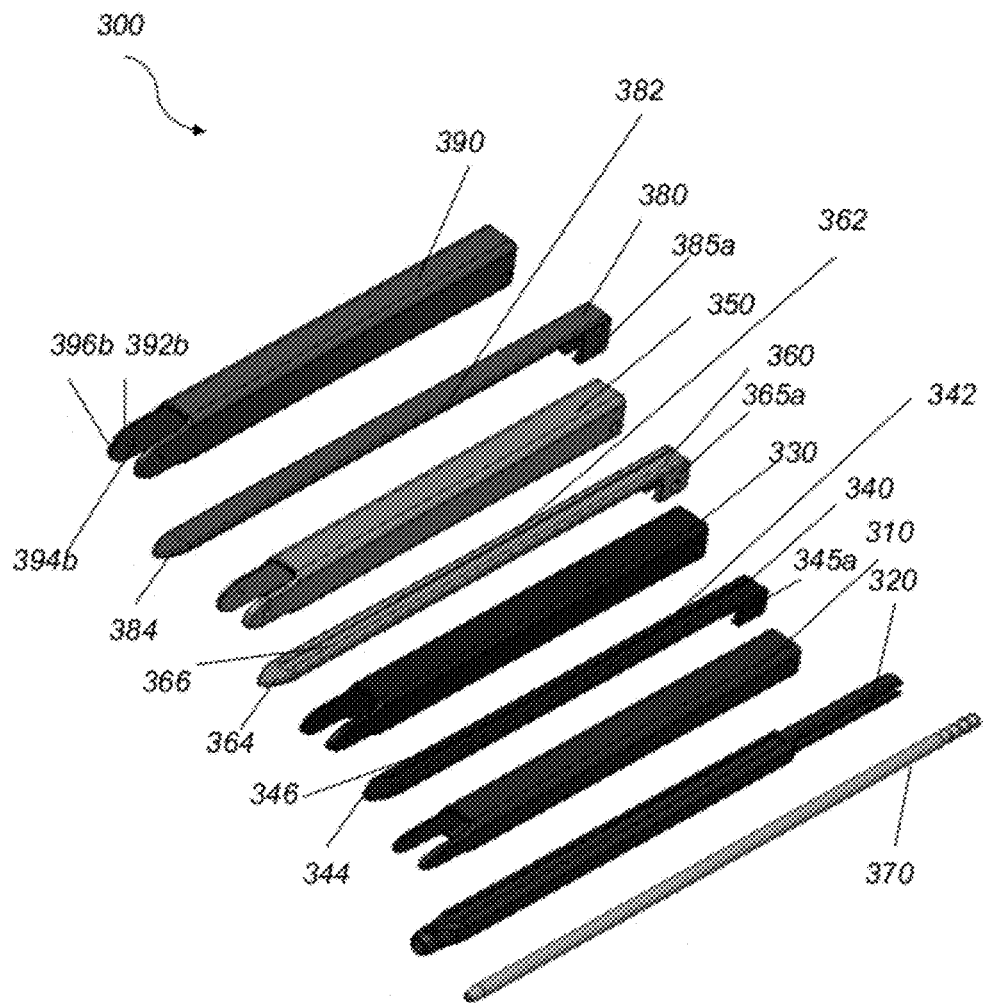
FIG. 1B is an exploded front view of the multi-component cannula system of FIG. 1A.

Referring to FIG. 1A, and FIG. 1B, access cannula system 300 includes a 14 mm working cannula 390 surrounding sequentially a 14 mm dilator 380, a 12 mm cannula 350, a 12 mm dilator 360, a 10 mm cannula 330, a 10 mm dilator 340, an 8 mm cannula 310, an 8 mm dilator 320 and a nerve probe dilator 370. Working cannula 390 includes an elongate tube 390 having a rectangular cross section and four side surfaces 390a, 390b (shown in FIG. 3B), 390c (shown in FIG. 4A), and 390d. Side surfaces 390a and 390b are opposite and parallel to each other and their distal ends terminate in parallel fork extensions 392a, 392b, respectively, that are tapered. Fork extensions 392a, 392b are rigid, are used for distraction purposes, and are dimensioned to fit in the intervertebral space. Fork extensions 392a, 392b include openings 394a, 394b (shown in FIG. 1B), respectively. The proximal ends of side surfaces 390a, 390b also include openings 398a, 398b (shown in FIG. 3B), respectively. Openings 394a, 394b and 398a, 398b function as fiduciary marks during fluoroscopy and are used for alignment purposes. Proximal end openings 398a, 398b are also used for gripping purposes. The 12 mm cannula 350, 10 mm cannula 330 and 8 mm cannula 310 are shaped similar to cannula 390 and are dimensioned to surround the corresponding 12 mm dilator 360, 10 mm dilator 340, and 8 mm dilator 320, respectively, and to be surrounded by the 14 mm cannula 390, 12 mm cannula 350, and 10 mm cannula 330, respectively, and by the 14 mm dilator 380, 12 mm dilator 360, and 10 mm dilator 340, respectively.

Figure 2A:
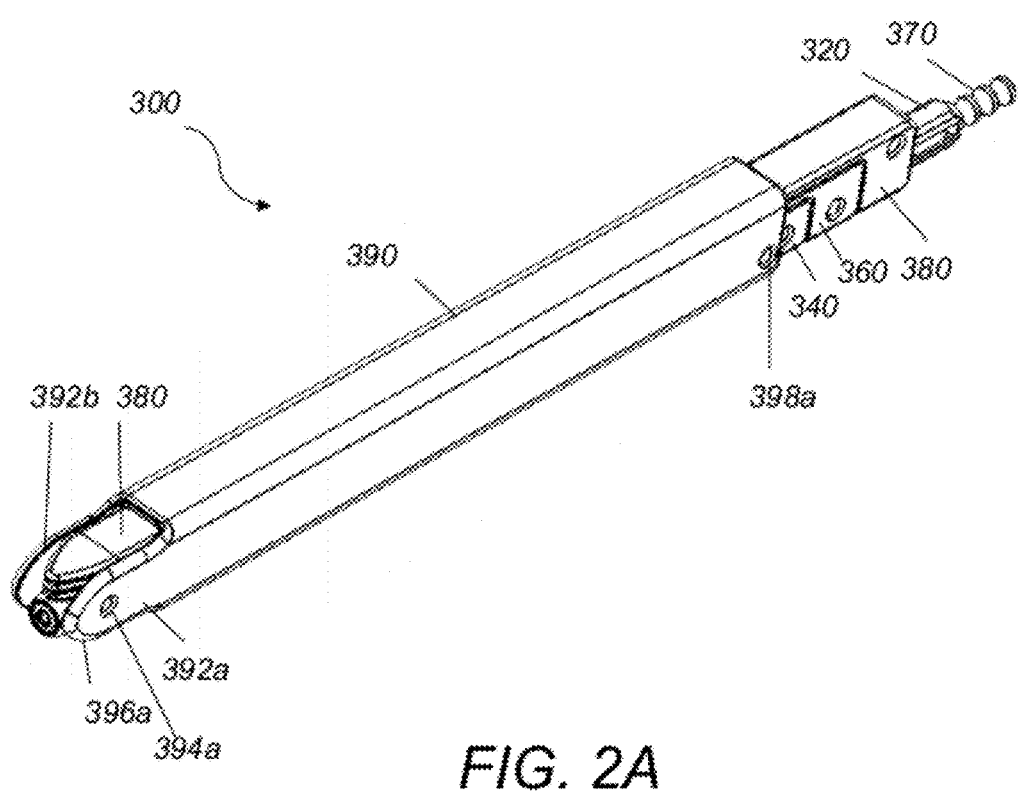
FIG. 2A is a front perspective view of a second embodiment of a multi-component cannula system.
Figure 2B:
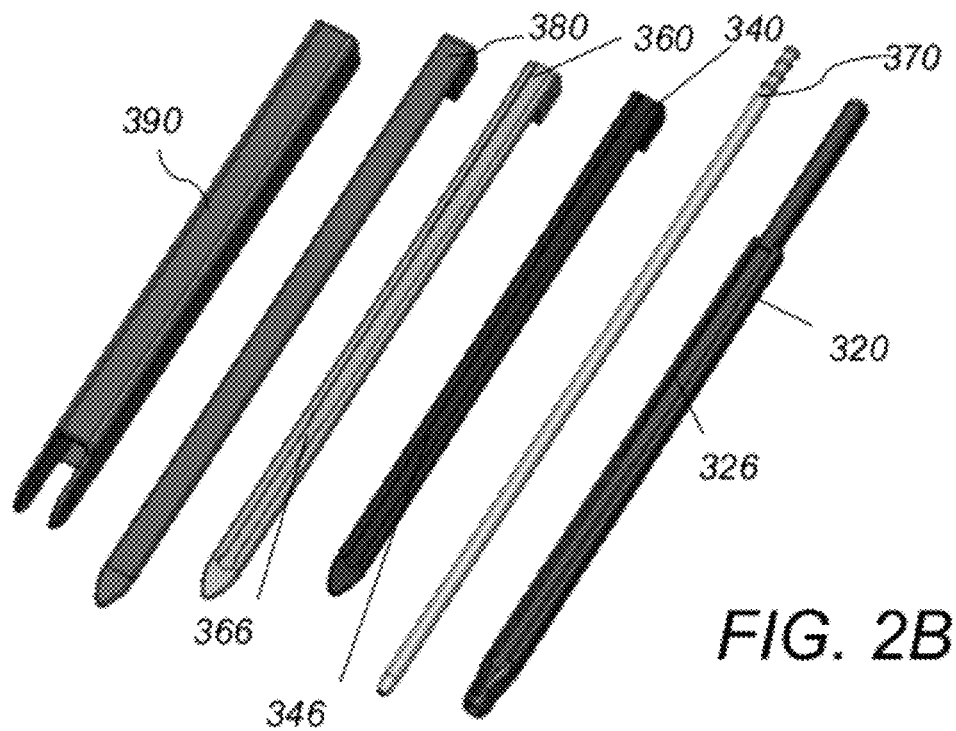
FIG. 2B is an exploded front view of the multi-component cannula system of FIG. 2A.
Figure 2C:
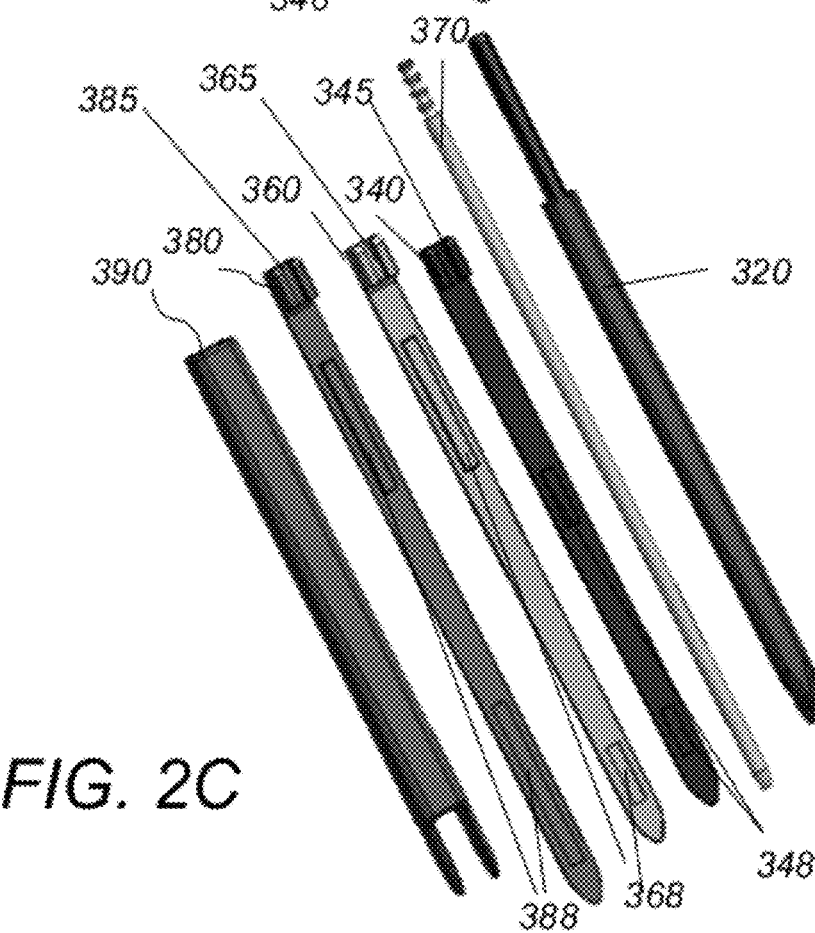
FIG. 2C is an exploded back view of the multi-component cannula system of FIG. 2A.
Figure 3A:
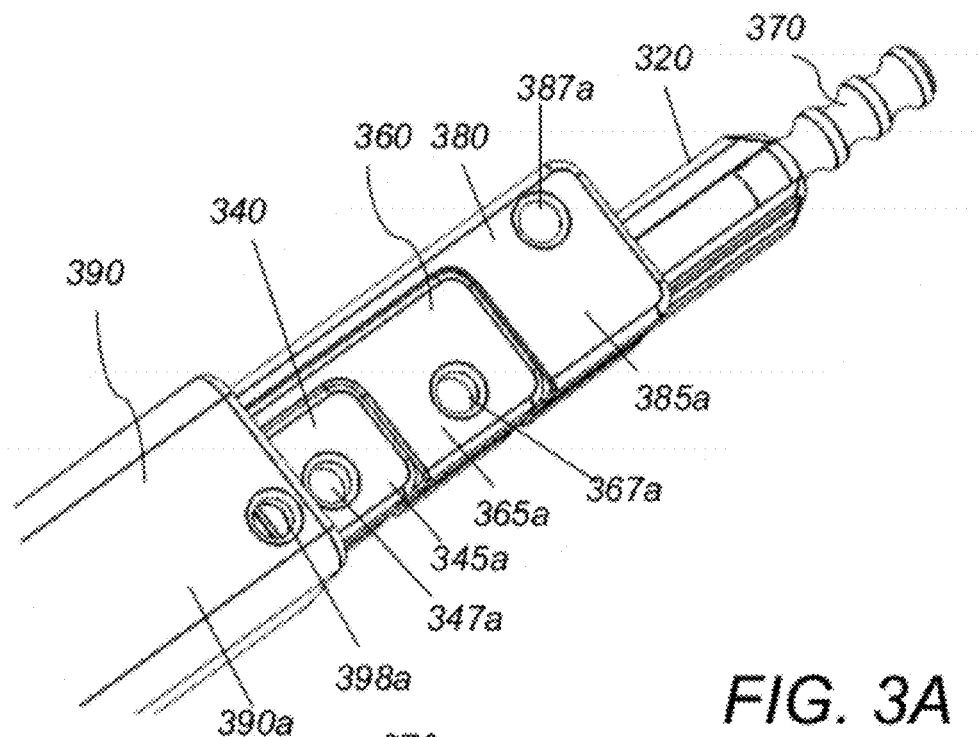
FIG. 3A is an enlarged right side view of the proximal end of the multi-component cannula system of FIG. 2A.
Figure 3B:
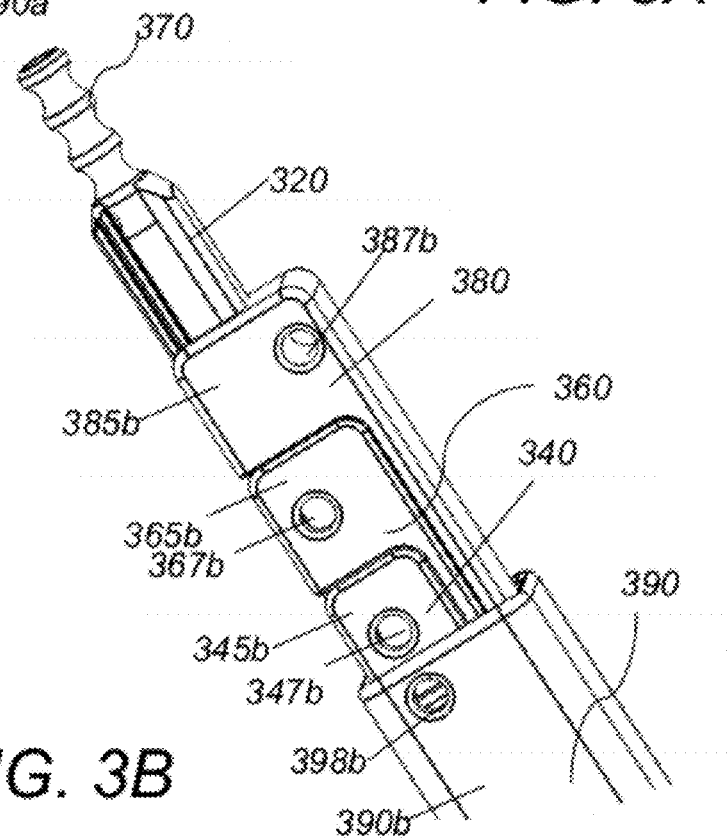
FIG. 3B is an enlarged left side view of the proximal end of the multi-component cannula system of FIG. 2A.
Figure 4A:
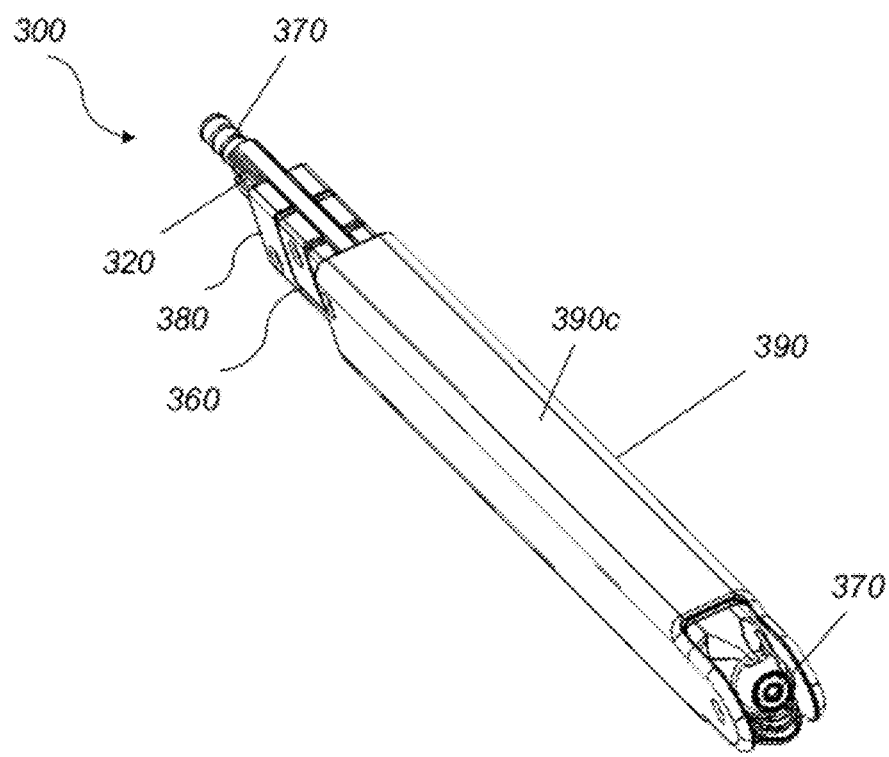
FIG. 4A is a back perspective view of the multi-component cannula system of FIG. 2A.
Figure 4B:
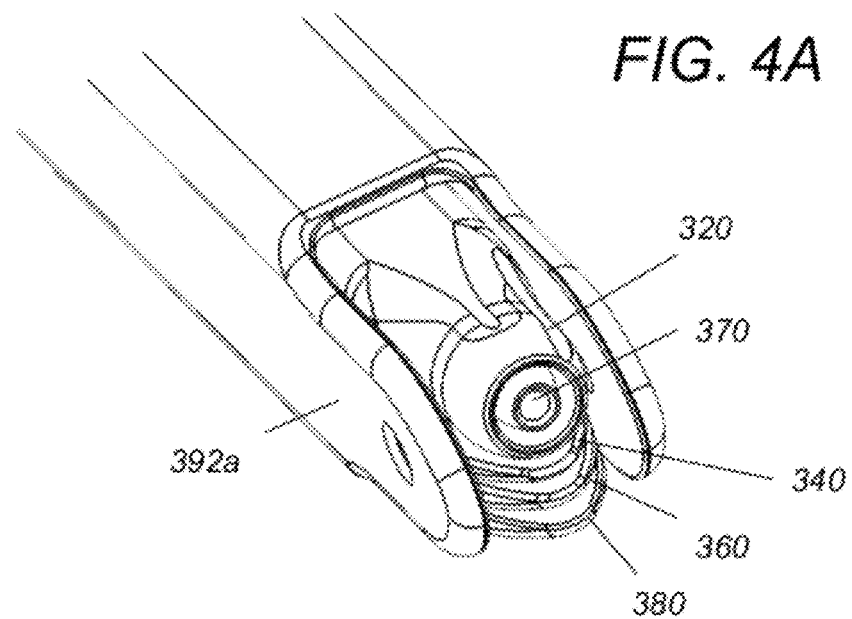
FIG. 4B is an enlarged view of the distal end of the multi-component cannula system of FIG. 4A.

Referring to FIG. 2A, FIG. 2B and FIG. 2C, in a second embodiment, access cannula system 300 includes a 14 mm working cannula 390 surrounding sequentially a 14 mm dilator 380, a 12 mm dilator 360, a 10 mm dilator 340, an 8 mm dilator 320 and a nerve probe dilator 370. In the embodiment of FIG. 1A and FIG. 2A, each dilator 380, 360, 340, includes a single elongated blade 382, 362, 342, respectively. Blades 382, 362, 342 have a tapered distal end and terminate into points 384, 364, 344, shown in FIG. 1B. The proximal ends 385, 365, 345 of blades 382, 362, 342 include two parallel extensions 385a-385b, 365a-365b, and 345a-345b, respectively, shown in FIG. 3A and FIG. 3B. Extensions 385a, 385b are spaced apart and a groove is formed between them. The groove is dimensioned so that the blade 382 can slide over the 12 mm dilator 360 and the end 385 can be stacked over the proximal end 365 of the 12 mm dilator 360, as shown in FIG. 3A and FIG. 3B. Similarly, extensions 365a, 365b are spaced apart and a groove is formed between them. The groove is dimensioned so that the blade 362 can slide over the 10 mm dilator 340 and the end 365 can be stacked over the end 345 of the 10 mm dilator 340, as shown in FIG. 3A and FIG. 3B. Similarly, extensions 345a, 345b are spaced apart and a groove is formed between them. The groove is dimensioned so that the blade 342 can slide over the 8 mm dilator 320 and the end 345 can be stacked over the 8 mm dilator 320, as shown in FIG. 3A and FIG. 3B. Extensions 385a, 385b include openings 387a, 387b, respectively, which are used for engaging a tool used to insert or remove the dilator 380. Similarly, extensions 365a, 365b include openings 367a, 367b, respectively, which are used for engaging a tool used to insert or remove the dilator 360. Similarly, extensions 345a, 345b include openings 347a, 347b, respectively, which are used for engaging a tool used to insert or remove the dilator 340. Referring to FIG. 2C, the bottom surfaces of blades 380, 360 and 340 include elongated tongue protrusions 388, 368 and 348, respectively. Referring to FIG. 2B, the top surfaces of blades 360, 340 and of dilator 320 include dovetail slots 366, 346 and 326, respectively. Tongue protrusions 388, 368 and 348 are dimensioned to engage and slide within the dovetail slots 366, 346 and 326, respectively, as the blades slide over each other and are stacked inside the working cannula 390.

Figures 5A, 5B, 5C:
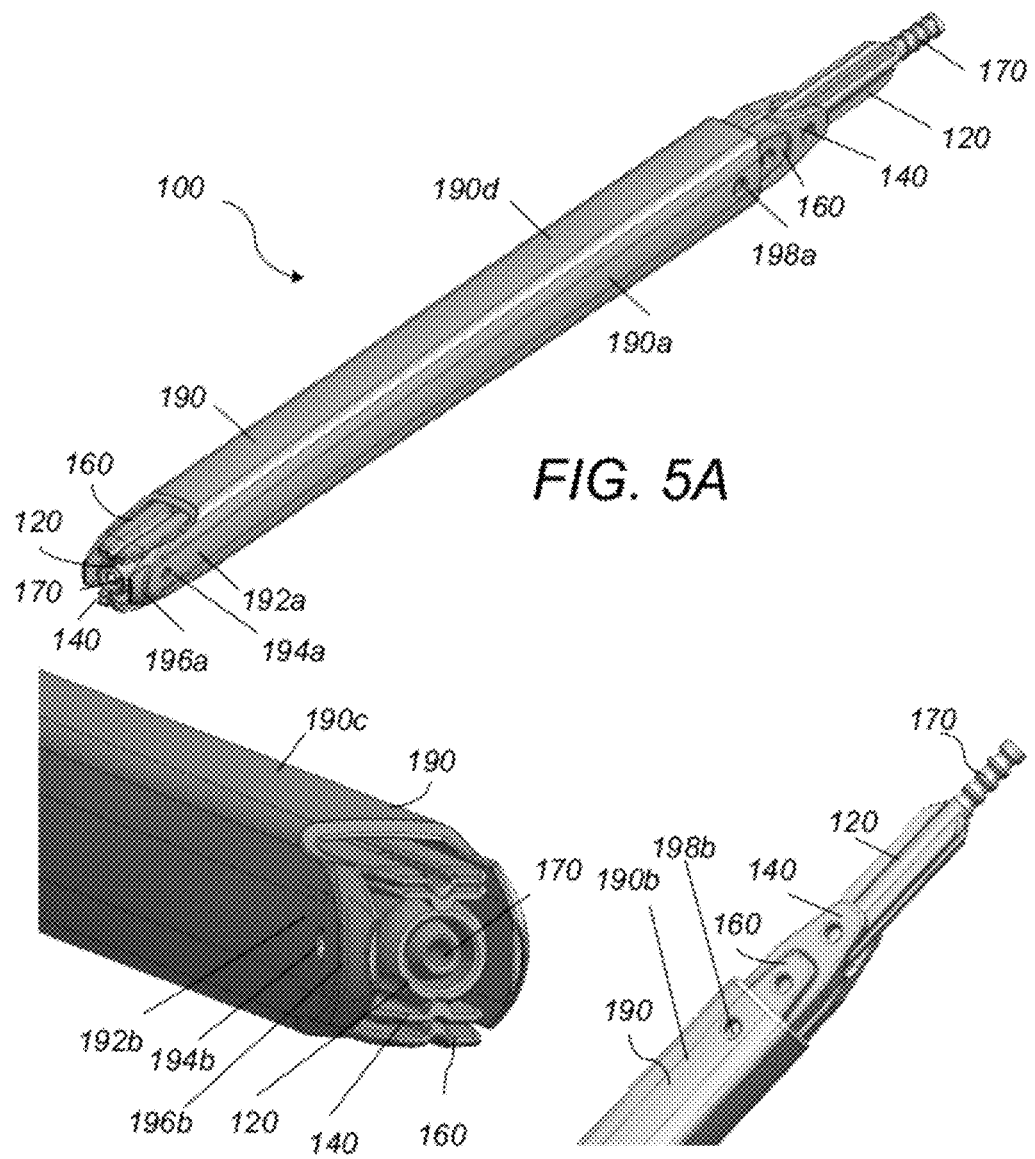
FIG. 5A is a front perspective view of a third embodiment of a multi-component cannula system.
FIG. 5B is an enlarged view of the distal end of the multi-component cannula system of FIG. 5A.
FIG. 5C is an enlarged view of the proximal end of the multi-component cannula system of FIG. 5A.
Figure 27A:
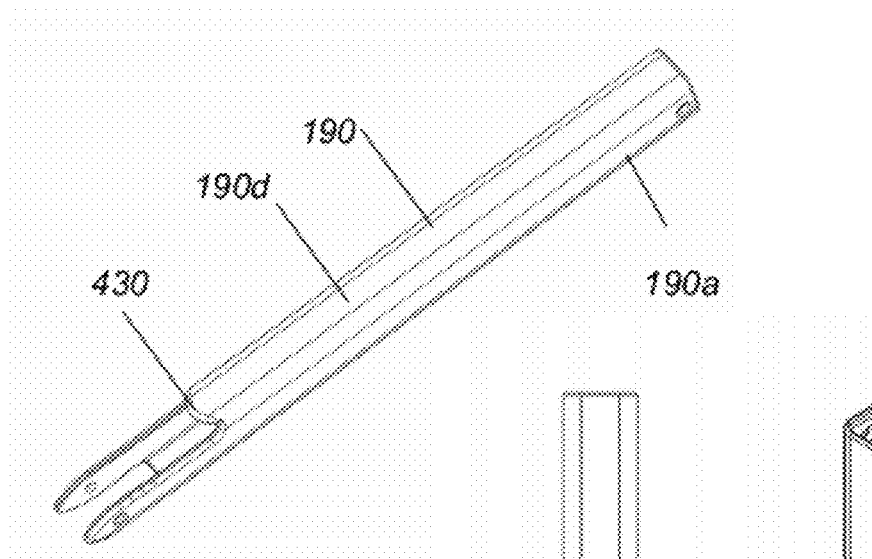
FIG. 27A depicts a front perspective view of another embodiment of the 14 mm cannula.
Figures 27B, 27C:
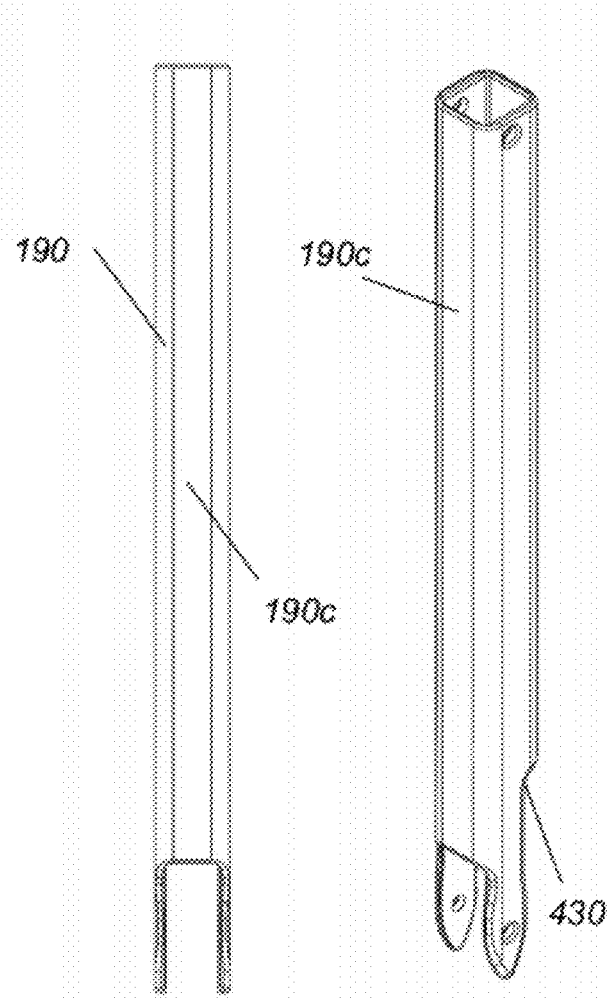
FIG. 27B is a side perspective view of the 14 mm cannula of FIG. 27A.
FIG. 27C is a back view of the 14 mm cannula of FIG. 27A.
Figure 29A:
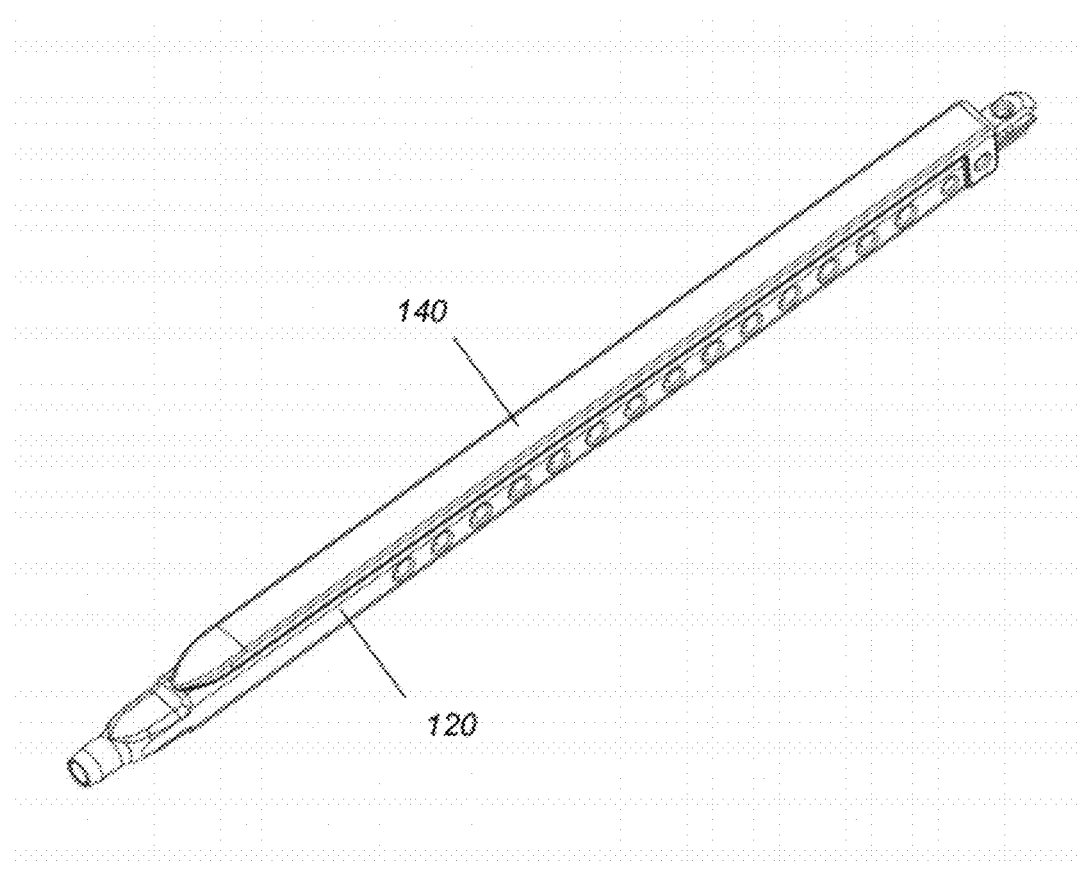
FIG. 29A depicts a front perspective view of another embodiment of the assembled 8 mm and 10 mm dilators.
Figure 29B:
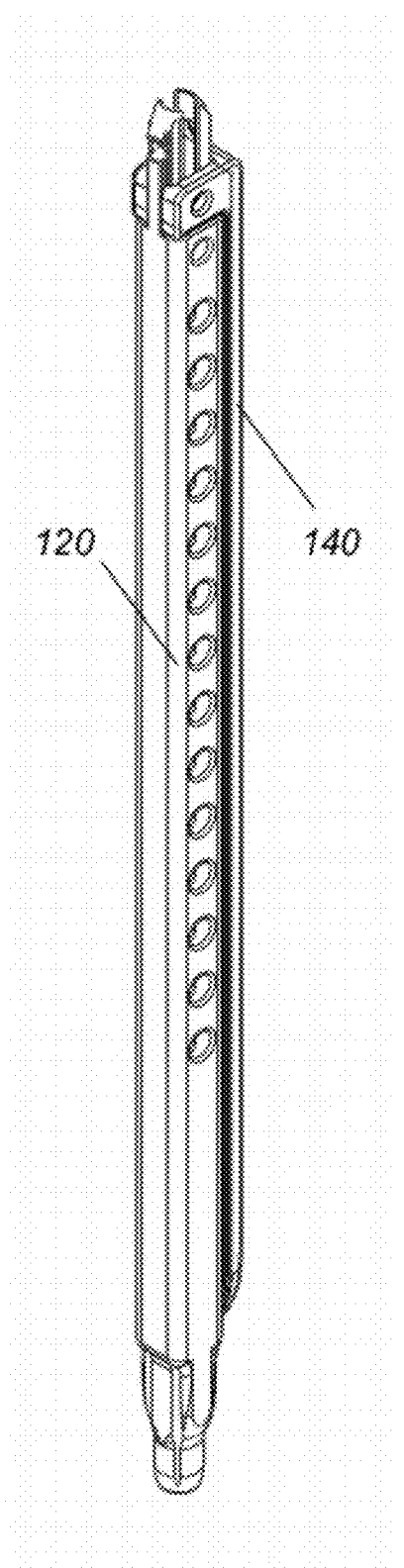
FIG. 29B depicts a back perspective view of the embodiment of the assembled 8 mm and 10 mm dilators of FIG. 29A.
Figure 29C:
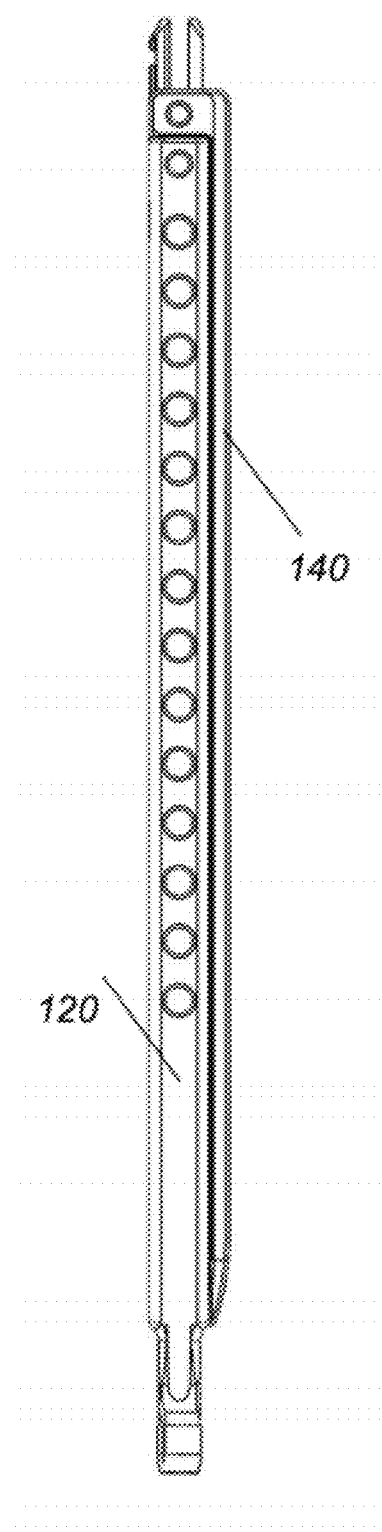
FIG. 29C depicts a side view of the embodiment of the assembled 8 mm and 10 mm dilators of FIG. 29A.
Figure 30A:
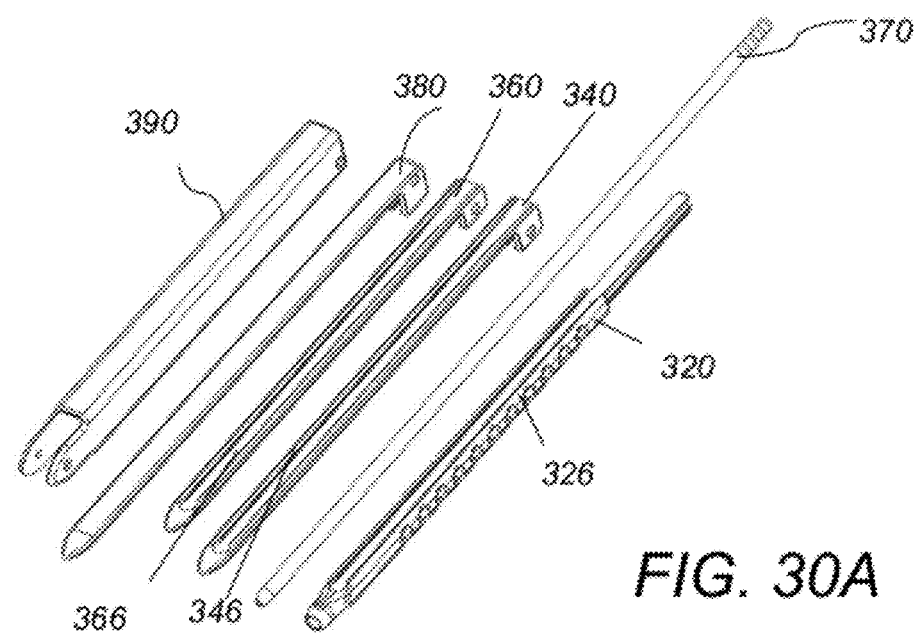
FIG. 30A depicts a back perspective view of another embodiment of the exploded multi-component system.
Figure 30B:
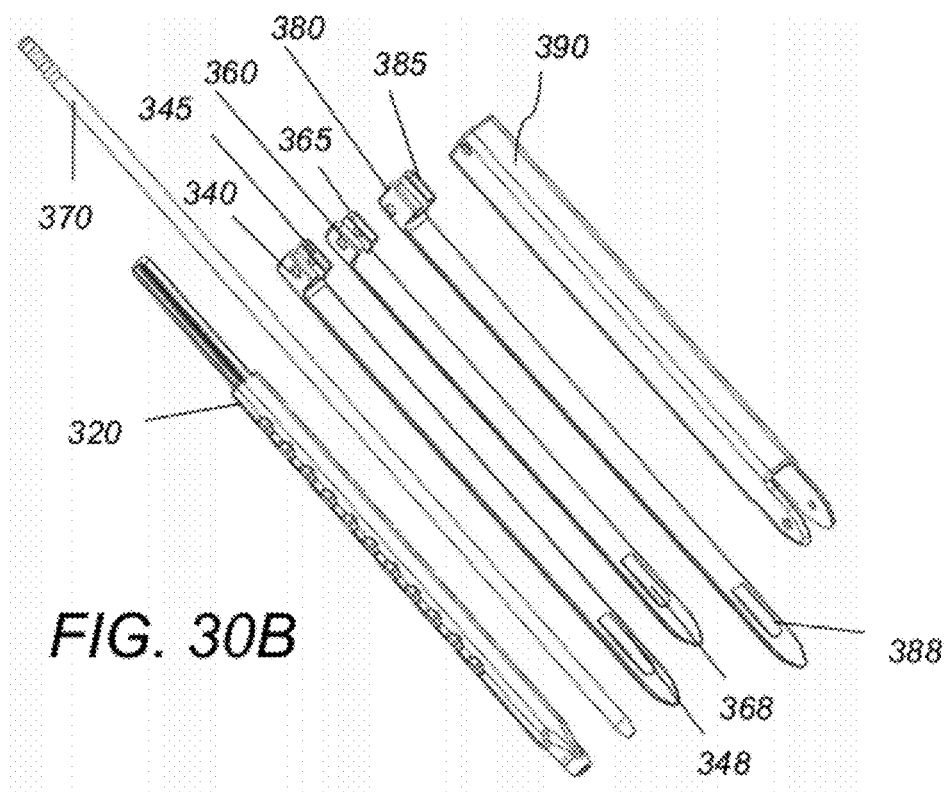
FIG. 30B depicts a front perspective view of the embodiment of the exploded multi-component system of FIG. 30A.

Referring to FIG. 5A, FIG. 5B, and FIG. 5C, in another embodiment, access cannula system 100 includes a 14 mm working cannula 190 surrounding sequentially a 12 mm dilator 160, a 10 mm dilator 140, an 8 mm dilator 120 and a nerve probe dilator 170. Working cannula 190 includes an elongate tube 190 having a rectangular cross section and four side surfaces 190a, 190b, 190c, and 190d. Side surfaces 190a and 190b are opposite and parallel to each other and their distal ends terminate in parallel fork extensions 192a, 192b, respectively. Fork extensions 192a, 192b are tapered and terminate into inverted trapezoids 196a, 196b, respectively. Fork extensions 192a, 192b are rigid, are used for distraction purposes, and are dimensioned to fit in the intervertebral space. Fork extensions 192a, 192b include openings 194a, 194b, respectively. Openings 194a, 194b function as fiduciary marks during fluoroscopy and are used for alignment purposes during fluoroscopy. The proximal ends of side surfaces 190a, 190b also include openings 198a, 198b, respectively. Openings 198a, 198b function as fiduciary marks during fluoroscopy and are used for alignment purposes and for gripping purposes. Side surfaces 190c and 190d are opposite and parallel to each other. In other embodiments, side surface 190d includes a cutout 430 at the distal end and has a shorter length than the opposite surface 190c, as shown in FIG. 27A-FIG. 27C. Cutout 430 allows the cannula to surround the inferior pedicle and to protect the nerve root that is on the opposite side of the cutout.

Figure 6A:
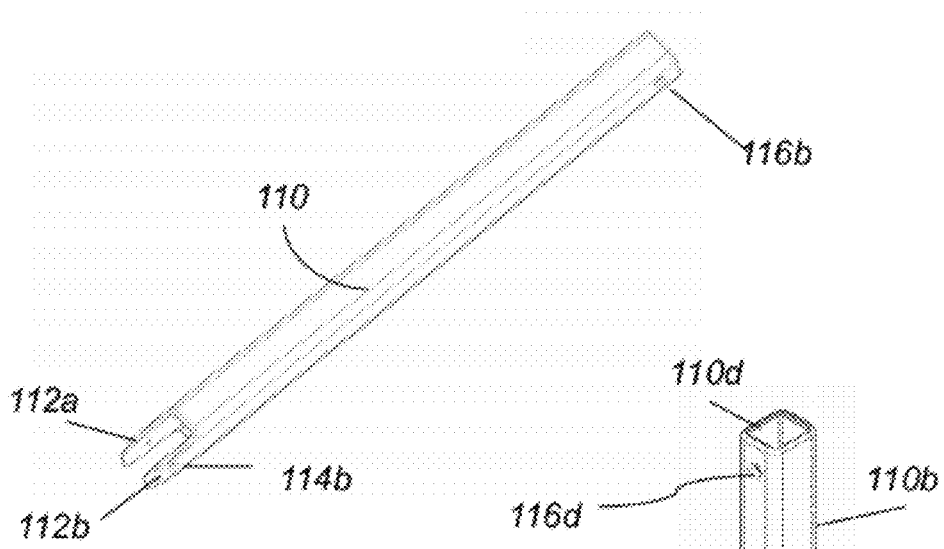
FIG. 6A is a perspective view of an 8 mm cannula of the multi-component cannula system of FIG. 5A.
Figure 6B:
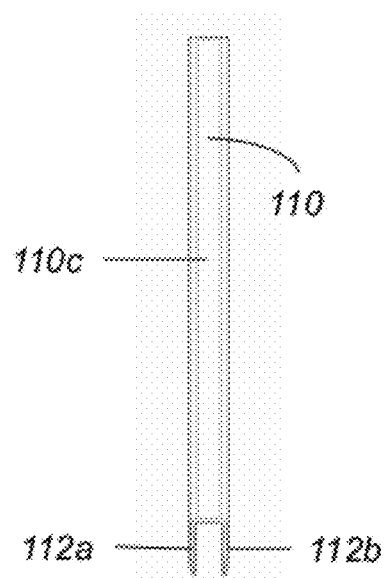
FIG. 6B is a front view of the 8 mm cannula of FIG. 6A.
Figure 6C:
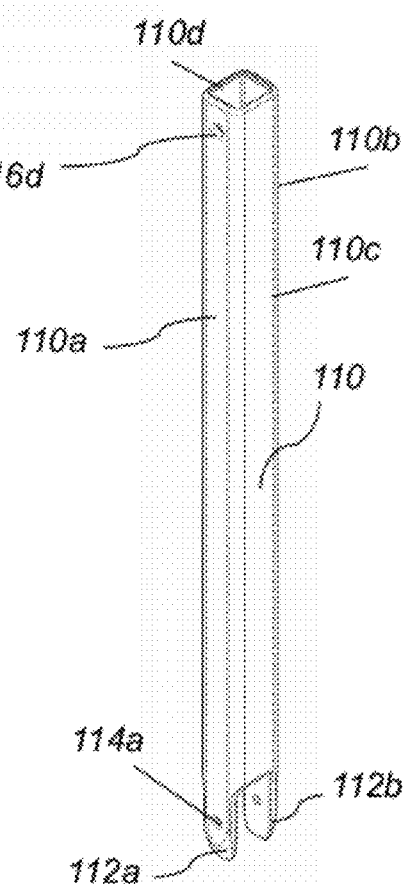
FIG. 6C is a front isometric view of the 8 mm cannula of FIG. 6A.

Referring to FIG. 6A-FIG. 6C, the 8 mm cannula 110 is shaped similar to cannula 190 and is dimensioned to surround the corresponding 8 mm dilator 120. Referring to FIG. 8A-FIG. 8C, the 10 mm cannula 130 is shaped similar to cannula 190 and is dimensioned to surround the corresponding 10 mm dilator 140. Referring to FIG. 10A-FIG. 10C, the 12 mm cannula 150 is shaped similar to cannula 190 and is dimensioned to surround the corresponding 12 mm dilator 160.

Referring to FIG. 7A-FIG. 7C, the 8 mm dilator 120 includes a cylindrical inner lumen 128 surrounded by rectangular outer surfaces 120a, 120b, 120c and 120d. Outer surfaces 120a 120b include grooves (dovetail slots) 126a, 126b, respectively, used to engage tongue protrusions 148a, 148b, respectively, of the 10 mm dilator 140, as will be described below. Dilator 120 has a cylindrical distal end 122, with a serrated edge 125. Dilator 120 also has a proximal end 124 that includes two elongated extensions 124a, 124b. Extensions 124a, 124b are parallel to each other and are separated by a distance corresponding to the diameter of the inner lumen. Dilator 120 also includes a second elongated through opening 127 used for accommodating a nerve probe, as shown in FIG. 7D and FIG. 7E. A nerve probe is used for detecting nerves in the vicinity of the dilator distal end 122 during the insertion of the dilator.

Referring to FIG. 9A-FIG. 9C, the 10 mm dilator 140 includes two parallel blades 142a, 142b that extend along the cannula axis 99 from a common proximal end 145 and have separated distal ends 141a, 141b, respectively. Distal ends 141a, 141b are tapered and terminate into inverted trapezoids 143a, 143b, respectively. The outer surfaces of blades 142a, 142b include grooves 146a, 146b, respectively. The inner surfaces of blades 142a, 142b include elongated tongue protrusions 148a, 148b, respectively. Tongue protrusions 148a, 148b are dimensioned to engage the corresponding outer surface grooves 126a, 126b of the 8 mm dilator 120. Proximal end 145 includes two tapered extensions 144a, 144b that are spaced apart from each other and parallel to each other. Extensions 144a, 144b extend along the cannula main axis 99 and are perpendicular to the blades 142a, 142b, respectively. Extensions 144a, 144b include openings 147a, 147b, respectively, used for engaging an insertion or removal tool.

Figure 11A:
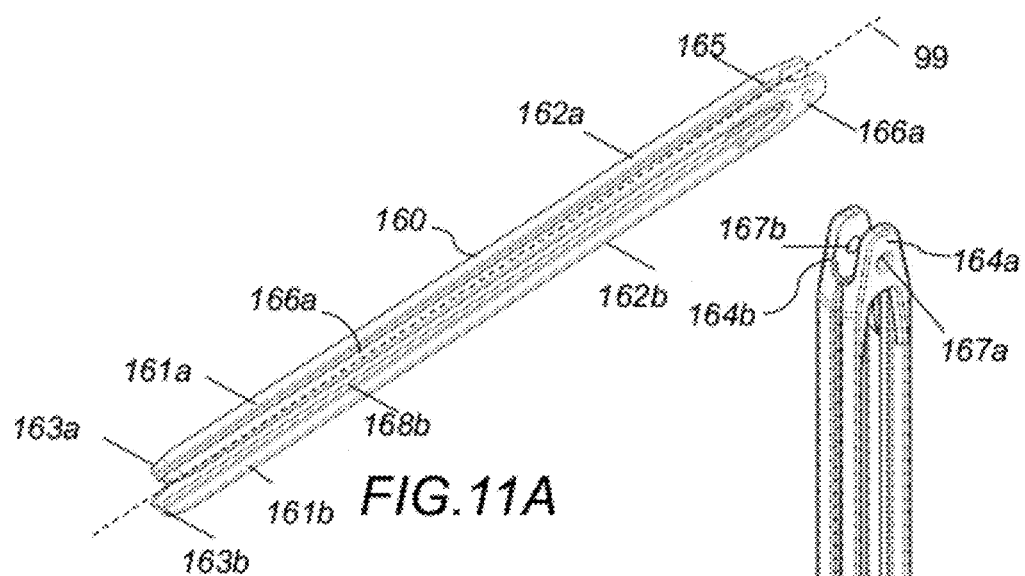
FIG. 11A is a perspective view of a 12 mm dilator of the multi-component cannula system of FIG. 5A.
Figure 11B:
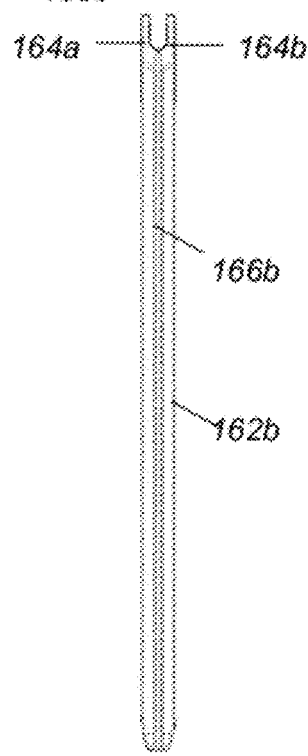
FIG. 11B is a front view of the 12 mm dilator of FIG. 11A.
Figure 11C:
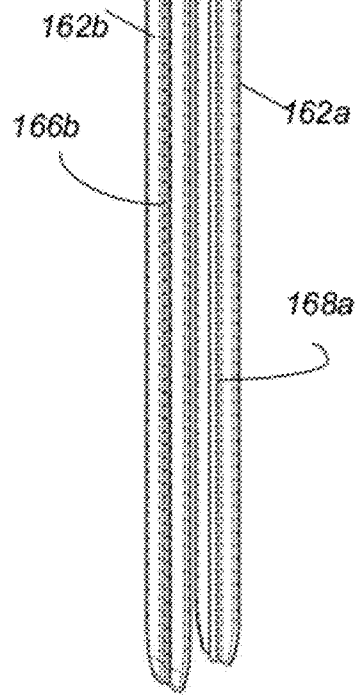
FIG. 11C is a front isometric view of the 12 mm dilator of FIG. 11A.

Referring to FIG. 11A-FIG. 11C, the 12 mm dilator 160 includes two parallel blades 162a, 162b that extend along the cannula axis 99 from a common proximal end 165 and have separated distal ends 161a, 161b, respectively. Distal ends 161a, 161b are tapered and terminate into inverted trapezoids 163a, 163b, respectively. The outer surfaces of blades 162a, 162b include grooves 166a, 166b, respectively. The inner surfaces of blades 162a, 162b include elongated tongue protrusions 168a, 168b, respectively. Tongue protrusions 168a, 168b are dimensioned to engage the corresponding outer surface grooves 146a, 146b of the 10 mm dilator 140. Proximal end 165 includes two tapered extensions 164a, 164b that are spaced apart from each other and parallel to each other. Extensions 164a, 164b extend along the cannula main axis 99 and are perpendicular to the blades 162a, 162b, respectively. Extensions 164a, 164b include opening 167a, 167b, respectively, used for engaging an insertion or removal tool.

Figures 12A, 12B:
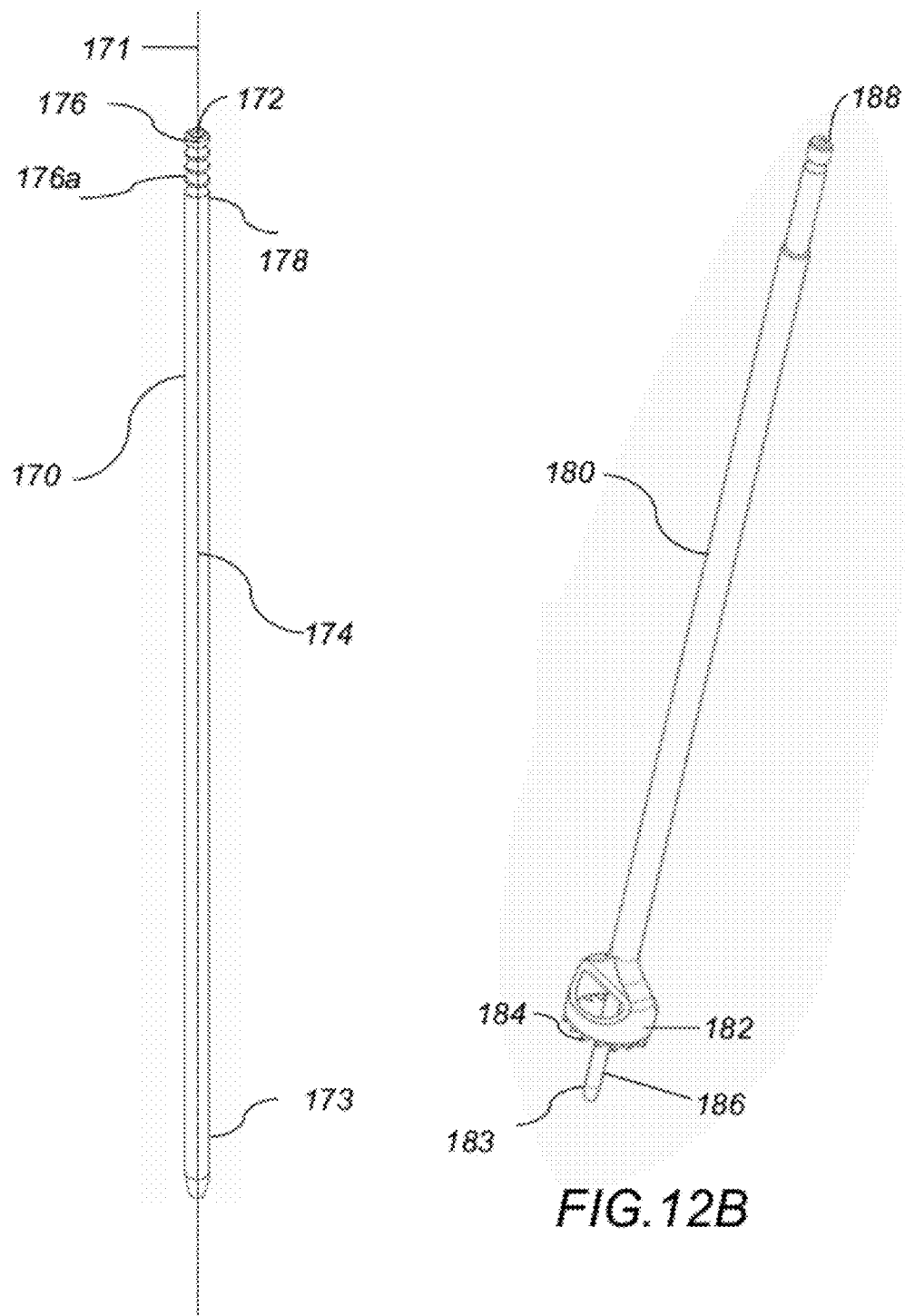
FIG. 12A is a front isometric view of the nerve probe dilator of FIG. 5A.
FIG. 12B is a front isometric view of a trephine drill.

Referring to FIG. 12A, nerve probe dilator 170 includes a cylindrical main shaft 174 extending along axis 171 and having a distal end 173, proximal end 176 and a lumen 172. Lumen 172 is dimensioned to receive nerve probe 175, shown in FIG. 13A. Distal end 173 has a conical shape and is used for tissue dilation purposes. Proximal end 176 has threads or circular protrusions 176a used for engaging a handle 179, shown in FIG. 13A. Referring to FIG. 12B, in another embodiment, nerve probe dilator 180 includes a trephine drill 182 surrounding the conical distal end 186. Trephine drill 182 includes teeth 184 used for drilling through bone, or cartilage.

Figure 13A:
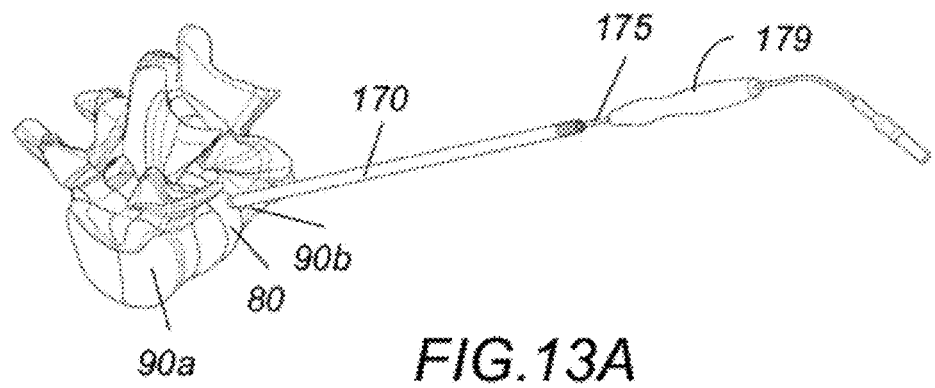
FIG. 13A depicts the step of inserting the nerve probe dilator and the nerve probe in the intervertebral space between two adjacent vertebras.

Referring to FIG. 13A, in operation, first a safe insertion trajectory is determined using active radiographic and optical imaging and the nerve probe 175 is inserted in the intervertebral space 80 between two adjacent vertebras 90a, 90b. Once a safe distance from any adjacent nerves has been determined, nerve probe dilator 170 is threaded over the nerve probe 175 and is impacted in the intervertebral space 80 with the nerve probe impactor 410, shown in FIG. 25A and FIG. 25B. Nerve probe impactor 410 has an elongated cylindrical body having a slot 412 extending the entire length of the elongated body, as shown in FIG. 25C and FIG. 25D. Slot 412 is dimensioned to slide over and accommodate the nerve probe 175.

Figure 13B:
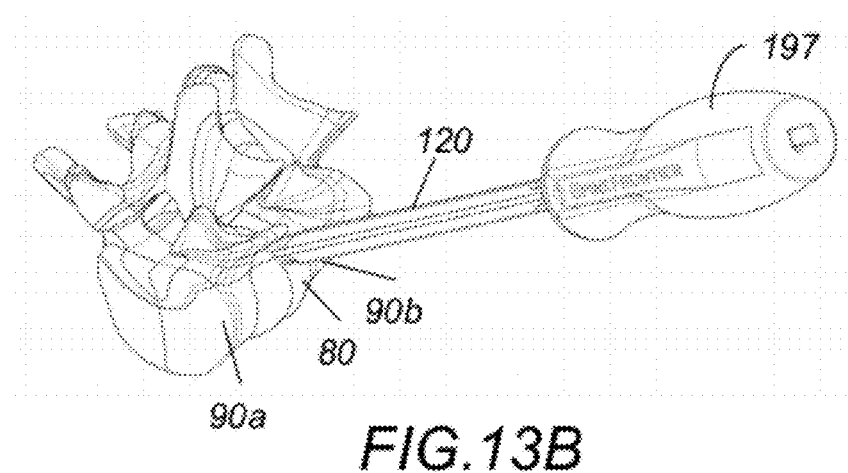
FIG. 13B depicts the step of inserting the 8 mm cannula over the nerve probe dilator.
Figure 13C:
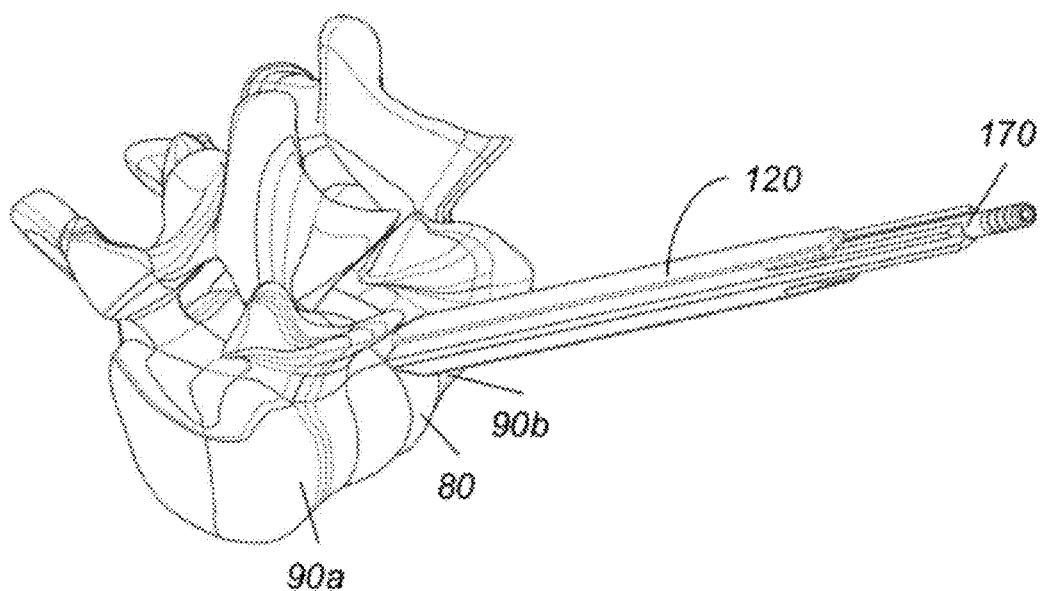
FIG. 13C depicts the step of inserting the 8 mm dilator.
Figure 14A:
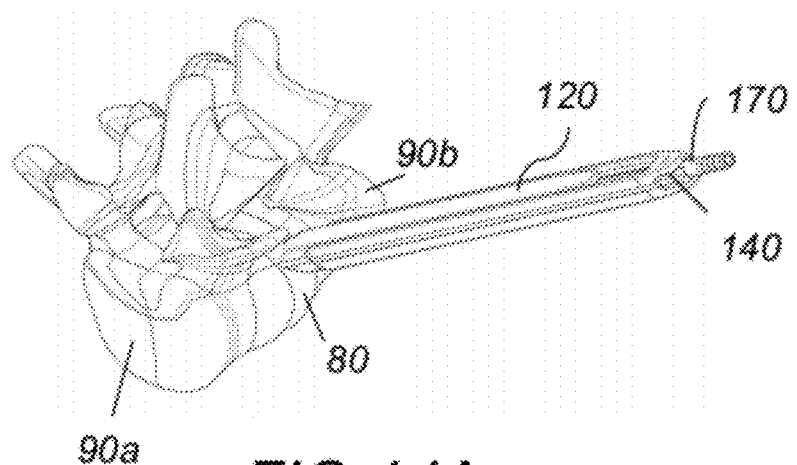
FIG. 14A depicts the step of inserting the 10 mm dilator.
Figure 14B:
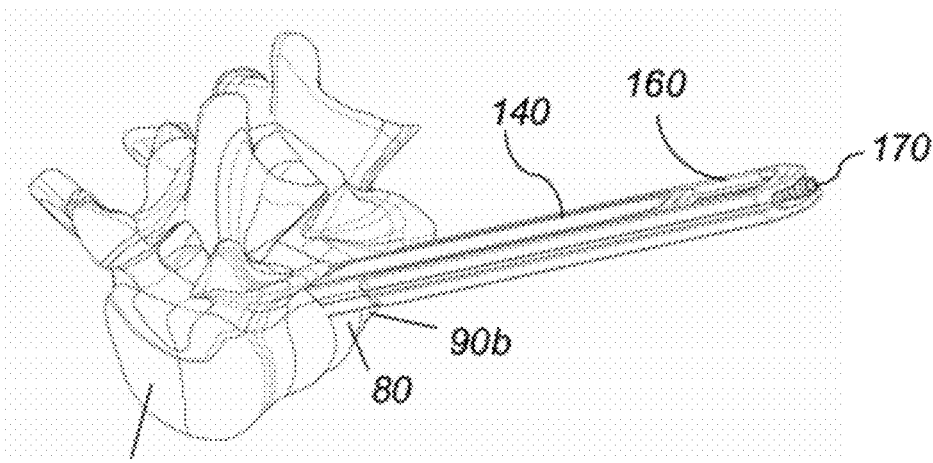
FIG. 14B depicts the step of inserting the 12 mm dilator.
Figure 14C:
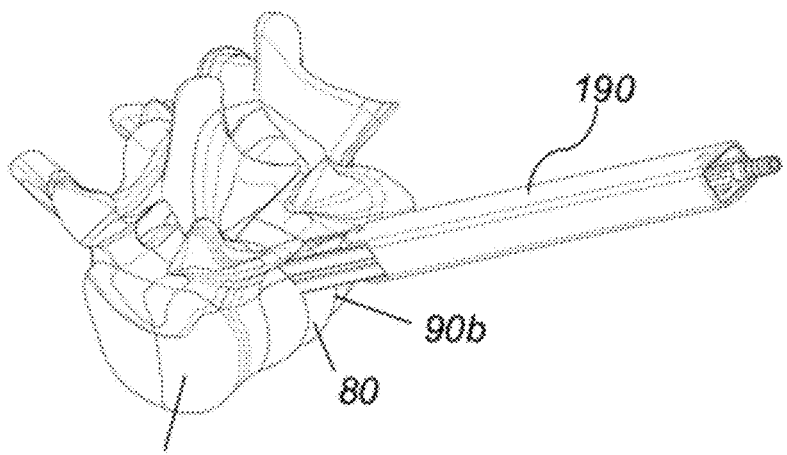
FIG. 14C depicts the step of inserting the working cannula.
Figure 15A:
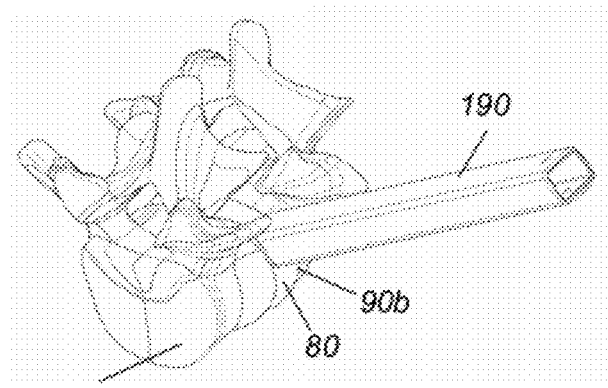
FIG. 15A depicts the working cannula inserted at an oblique direction in the intervertebral area between a first vertebra and a second vertebra.
Figure 15B:
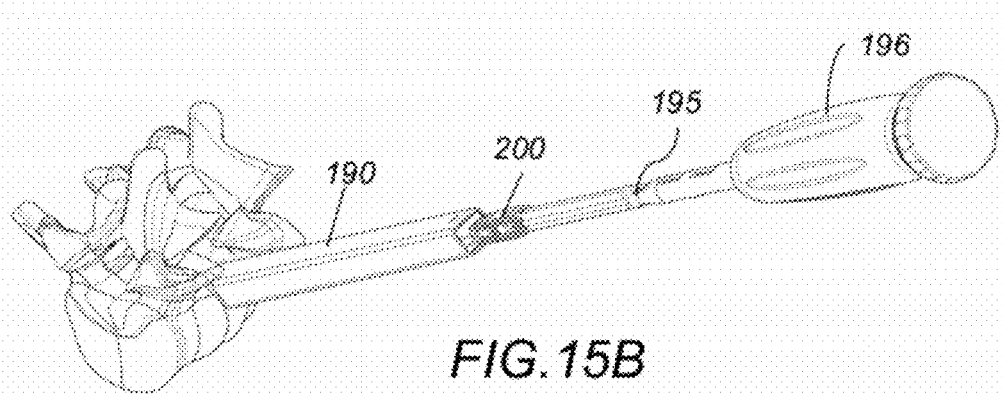
FIG. 15B depicts the step of inserting the intervertebral implant through the working cannula of FIG. 15A.
Figure 15C:
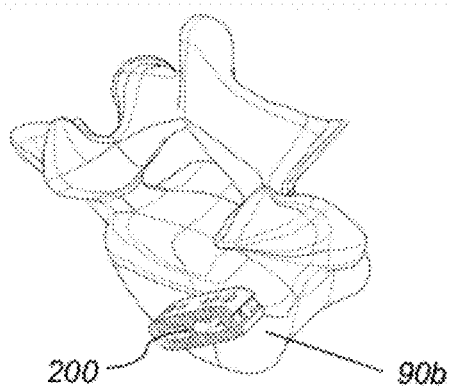
FIG. 15C depicts the inserted intervertebral implant in the intervertebral space.
Figure 15D:
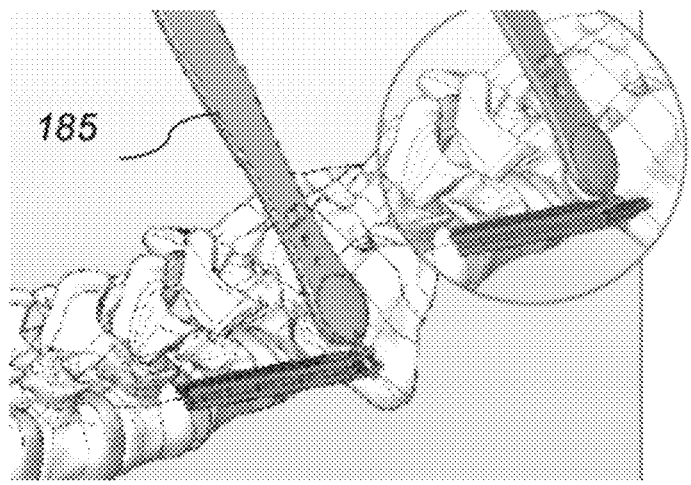
FIG. 15D depicts the step of impacting the inserted dilator.
Figure 15E:
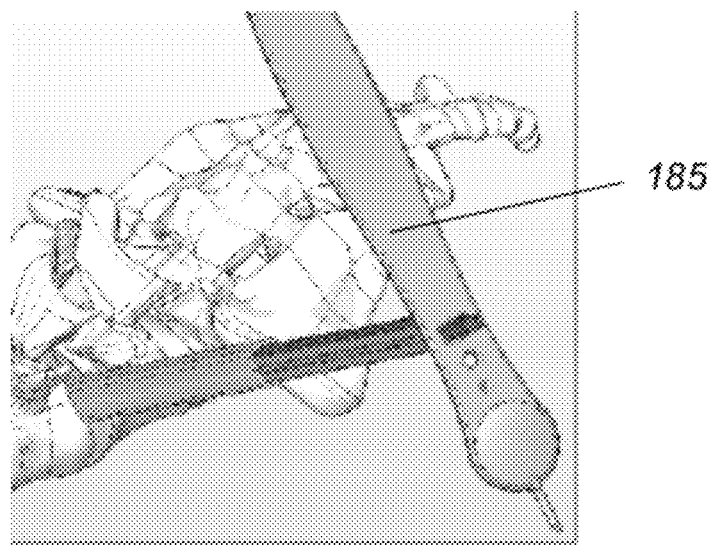
FIG. 15E depicts the step of removing the inserted dilator.

Next, the 8 mm dilator 120 is attached to a handle 197 and is slid over the nerve probe dilator 170, as shown in FIG. 13B. The area within the 8 mm dilator range is probed with the nerve probe to determine a safe distance from any adjacent nerves and then the 8 mm dilator is impacted in the intervertebral space 80, as shown in FIG. 13C. If the height of the intervertebral implant 200 is smaller than the opening achieved with the 8 mm dilator 120, an 8 mm cannula 110 is inserted over the 8 mm dilator, the 8 mm dilator is removed and the implant 200 is inserted in the intervertebral opening. If the height of the intervertebral implant 200 is larger than the opening achieved with the 8 mm dilator 120, the 10 mm dilator 140 is impacted over the 8 mm dilator in the intervertebral space 80 with the impactor 185, as shown in FIG. 14A, FIG. 15D and FIG. 15E. Impactor 185 has a tip 187 that is inserted in openings 147a, 147b of the 10 mm dilator, as shown in FIG. 15D. Again, the height of the intervertebral implant 200 is checked against the achieved opening, and if it is smaller than the opening, a 10 mm cannula 130 is inserted over the 10 mm dilator, the 8 mm dilator and the 10 mm dilator are removed and the implant 200 is inserted in the intervertebral opening. If the height of the intervertebral implant 200 is still larger than the opening achieved with the 10 mm dilator 140, the 12 mm dilator 160 is impacted over the 10 mm dilator in the intervertebral space 80, as shown in FIG. 14B. The process repeats until an opening that accommodates the intervertebral implant 200 is achieved. At that point, a working cannula 190 is impacted into the intervertebral space 80 with impactor handle 440, as shown in FIG. 28A-FIG. 28B and FIG. 15A, and all dilators are removed with tool 185, as shown in FIG. 15F. Impactor handle 440 has a hollow body with a rectangular cross section and is dimensioned to slide over the proximal end of cannula 190, as shown in FIG. 28B. Next, intervertebral implant 200 is inserted through the working cannula 190 and is placed in the intervertebral opening, as shown in FIG. 15B and FIG. 15C. All of the above mentioned operational steps are guided through fluoroscopic and optical imaging.

Figure 16A:
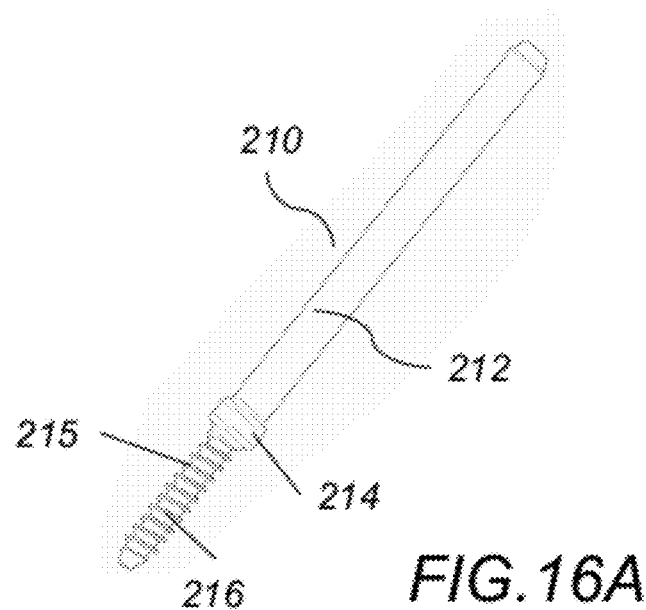
FIG. 16A is a perspective view of a distraction pin.
Figure 16B:
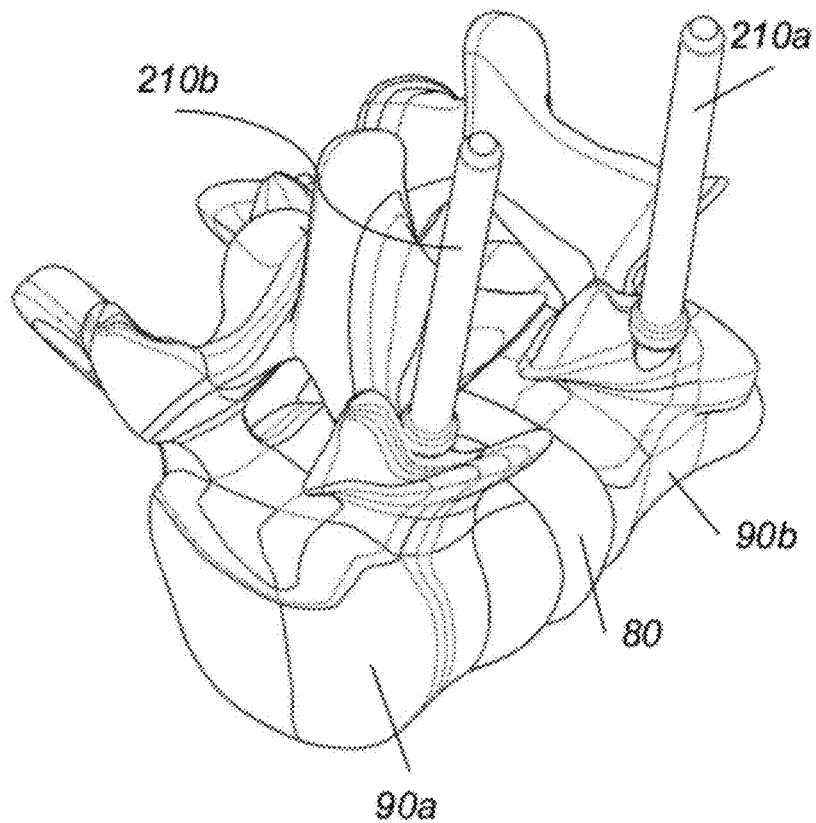
FIG. 16B depicts two distraction pin inserted in the pedicles of two adjacent vertebras.
Figure 17A:
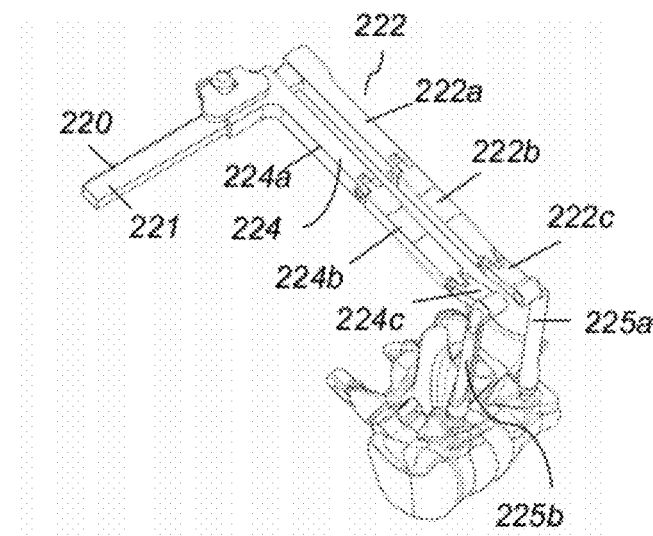
FIG. 17A depicts the step of inserting a distractor over the two distraction pins of FIG. 16B.
Figure 17B:
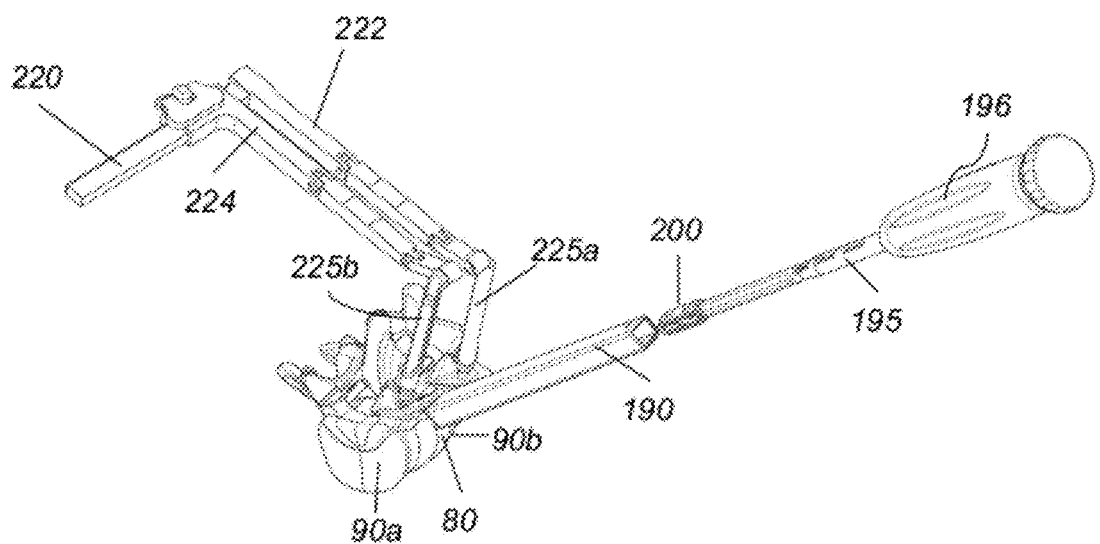
FIG. 17B depicts the step of inserting an intervertebral spacer through the working cannula in the distracted vertebras of FIG. 17A.
Figure 18:
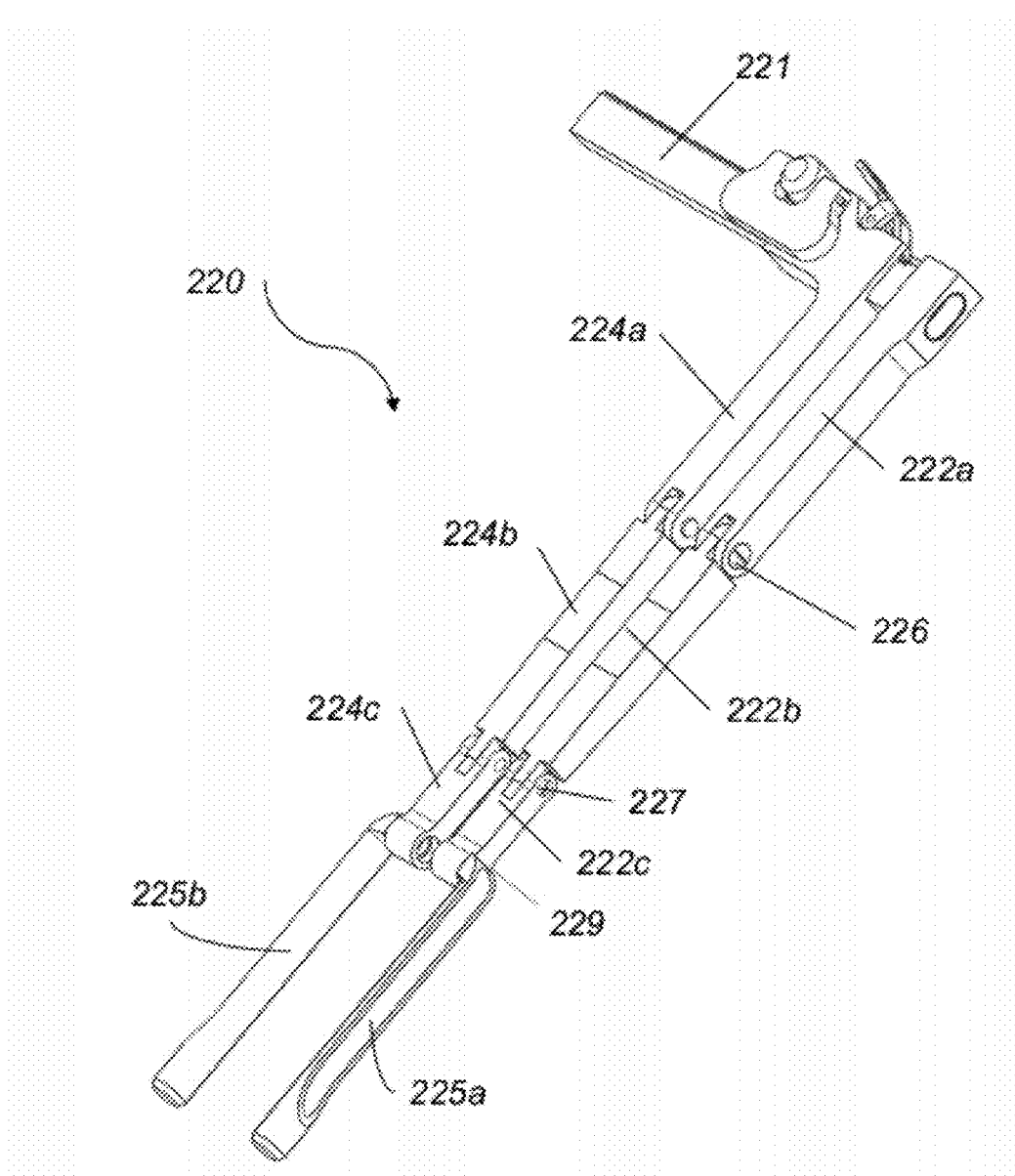
FIG. 18 is a perspective view of the distractor of FIG. 17A.
Figure 19A:
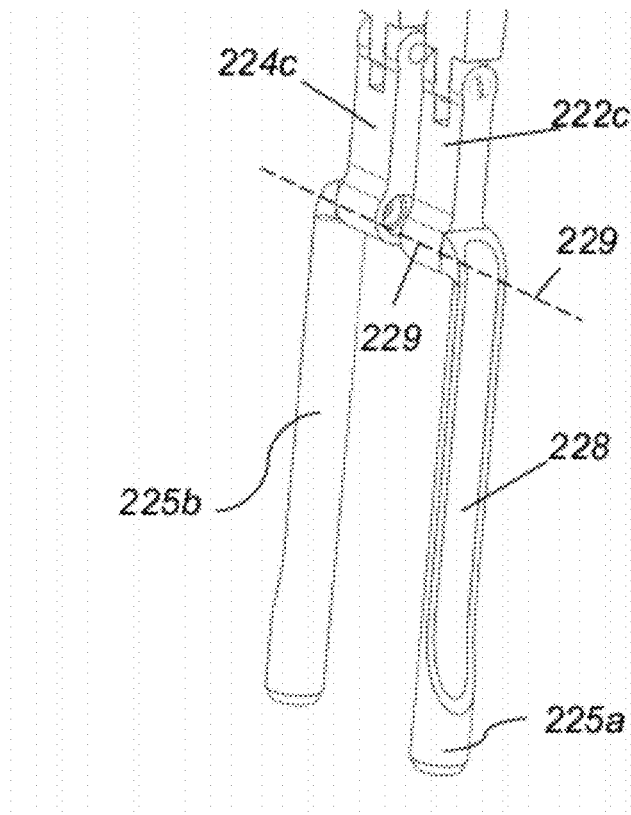
FIG. 19A is an enlarged perspective view of the distractor legs of the distractor of FIG. 18.
Figure 19B:
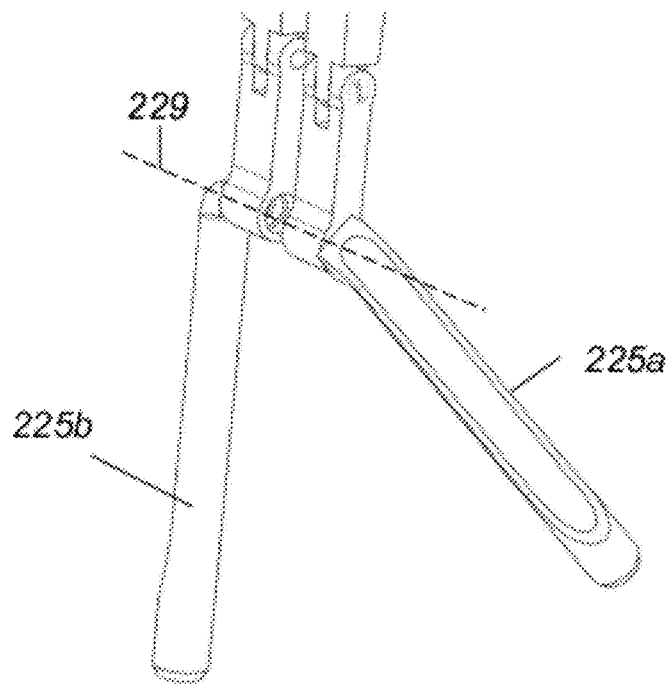
FIG. 19B is an enlarged perspective view of the distractor legs of FIG. 19A with one leg pivoted at an angle.
Figure 20A:
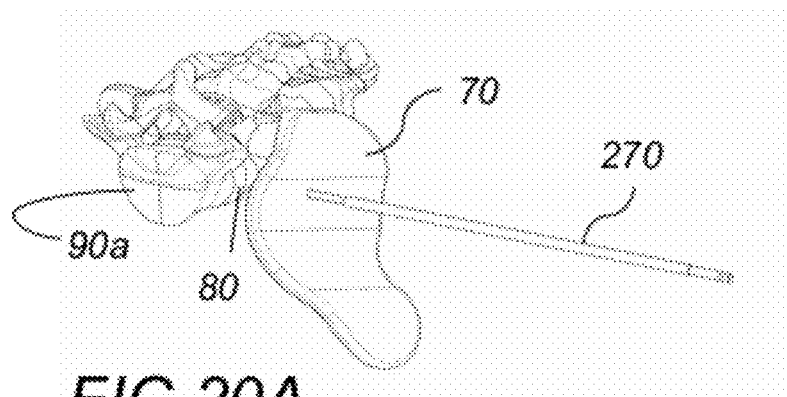
FIG. 20A depicts the step of inserting a solid awl in the intervertebral space between two adjacent vertebras through the iliac crest.
Figure 20B:
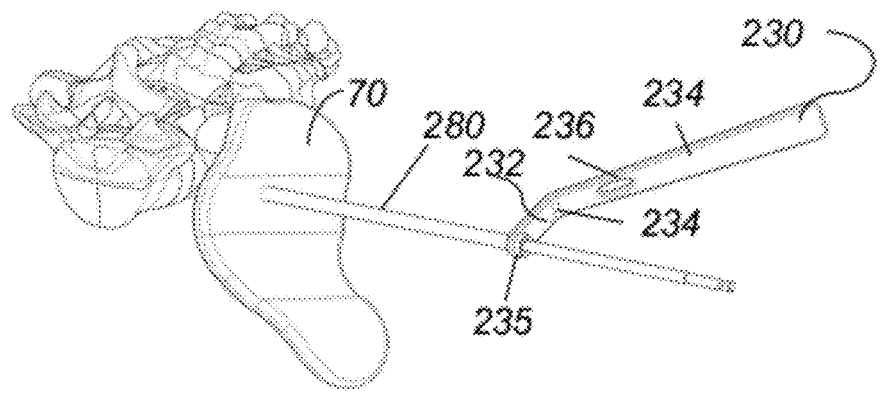
FIG. 20B depicts the step of inserting a tissue protector over the solid awl of FIG. 20A.
Figure 20C:
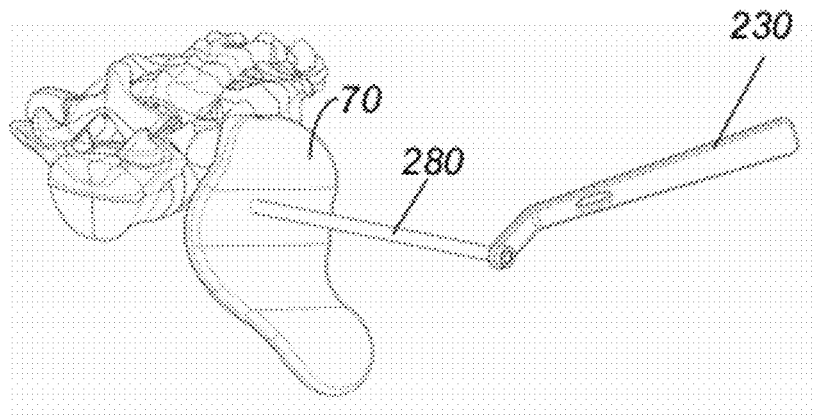
FIG. 20C depicts the step of impacting the tissue protector of FIG. 20B.
Figure 21A:
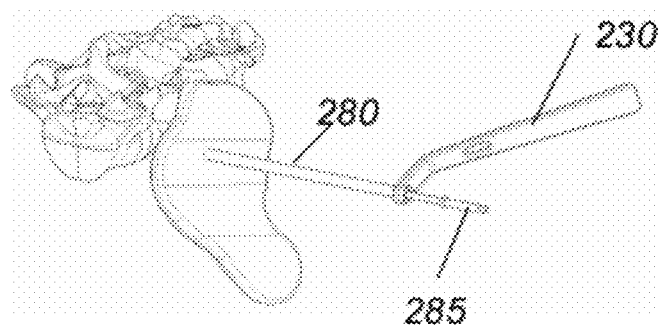
FIG. 21A depicts the step of removing the tissue protector of FIG. 20B.
Figure 21B:
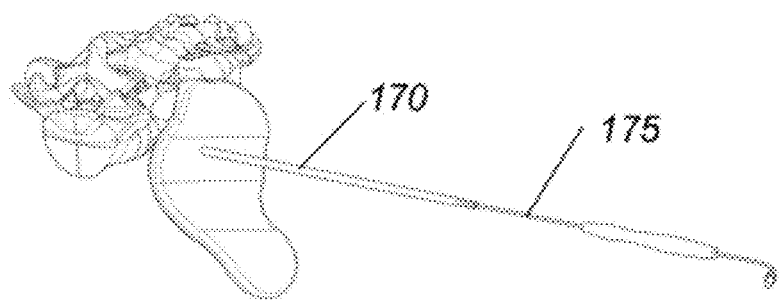
FIG. 21B depicts the step of inserting the nerve probe dilator.
Figure 21C:
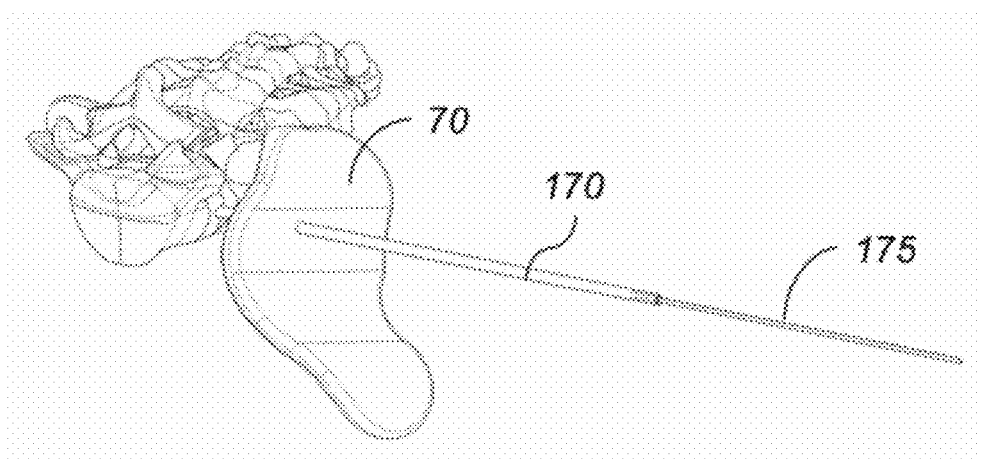
FIG. 21C depicts the step of inserting the nerve probe.
Figure 22A:
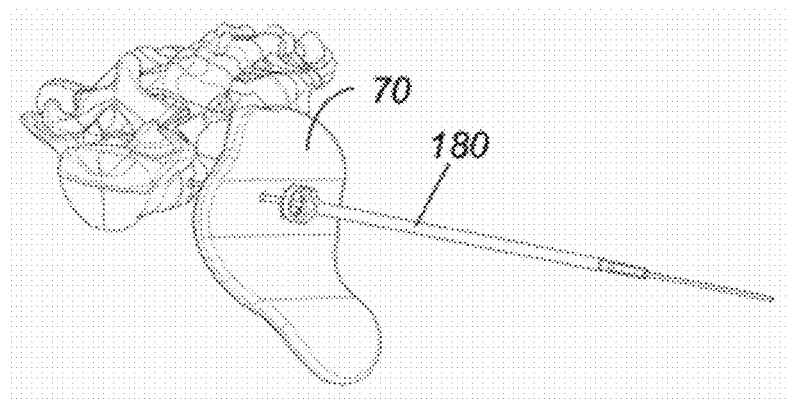
FIG. 22A depicts the step of inserting the trephine drill.
Figure 22B:
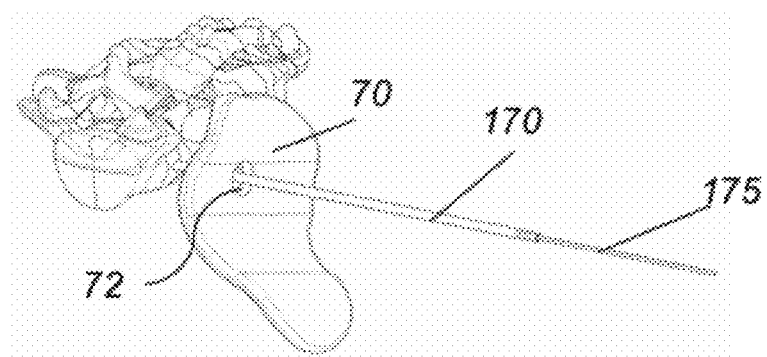
FIG. 22B depicts the opening in the iliac crest that was drilled with the trephine drill of FIG. 22A.
Figure 22C:
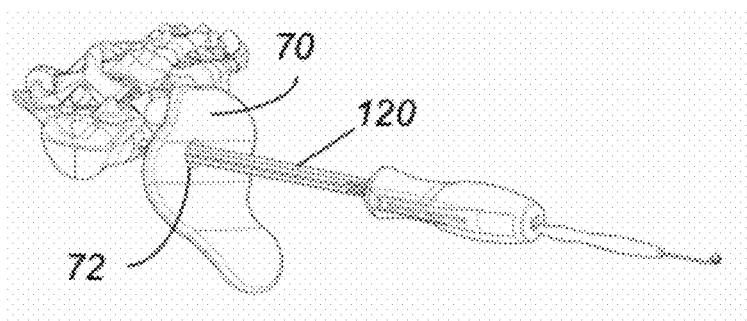
FIG. 22C depicts the step of inserting the 8 mm dilator.
Figure 23A:
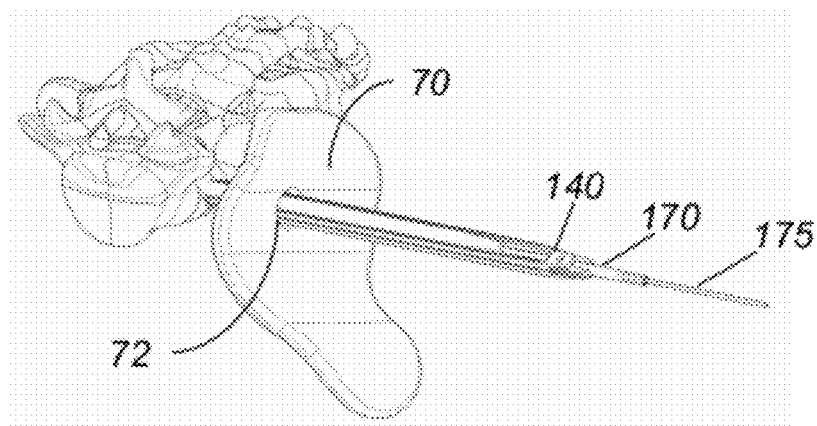
FIG. 23A depicts the step of inserting the 10 mm dilator.
Figure 23B:
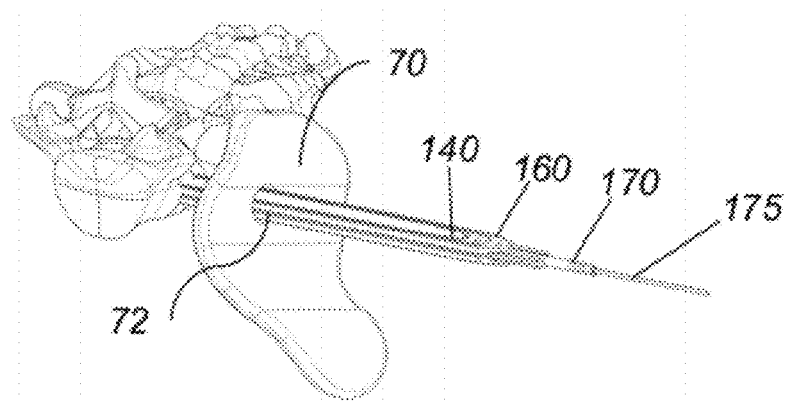
FIG. 23B depicts the step of inserting the 12 mm dilator.
Figure 23C:
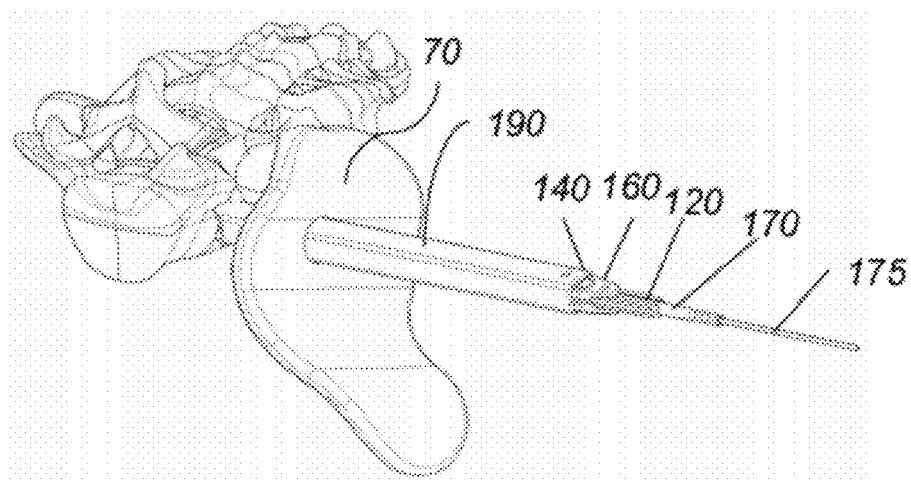
FIG. 23C depicts the step of inserting the working cannula.

In some operations, the adjacent vertebras 90a, 90b need to be distracted prior to the placement of the intervertebral implant 200 in the intervertebral space 80. Referring to FIG. 16A and FIG. 16B, two distractor pins 210a, 210b are inserted in first locations of the adjacent vertebras 90a, 90b, respectively. Distractor pin 210 includes an elongated shaft 212 that has a threaded distal end 216. The threaded distal end 216 is inserted in the desired vertebral location. Next, a distractor 220 is used to spread the inserted distractor pins 210a, 210b apart. Referring to FIG. 17A, distractor 220 includes a fixed carrier leg 222 and a movable carrier leg 224. Movable carrier leg 224 moves along track 221 that extends from the proximal end 222e of the fixed carrier leg 222. Fixed carrier leg 222 includes components 222a, 222b, and 222c that are hingably connected to each other. Movable carrier leg 224 includes components 224a, 224b, and 224c that are hingably connected to each other. Tubular pin components 225a and 225b extend from and are pivotally connected to the distal ends of components 222c and 224c, respectively. Tubular pin components 225a, 225b are dimensioned to slide over the distractor pin shafts 212 and they can pivot up to 360 degrees around axis 229 independent from each other, as shown in FIG. 19A. and FIG. 19B. In operation, tubular pin components 225a, 225b are placed over distractor shafts 212a, 212b and then the movable carrier leg is translated along track 221 and set at the desired distraction length. Next, an opening is impacted in the intervertebral disk space 80 with the above mentioned cannula system and then the intervertebral implant 200 is inserted in the opening, as shown in FIG. 17B.

Figure 24A:
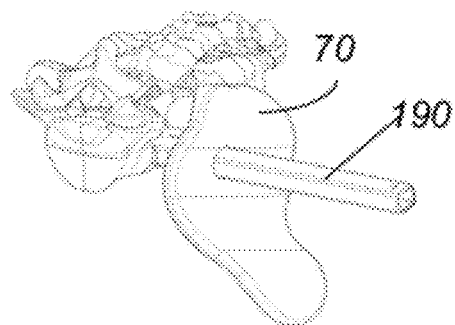
FIG. 24A depicts the step of removing all dilators.
Figure 24B:
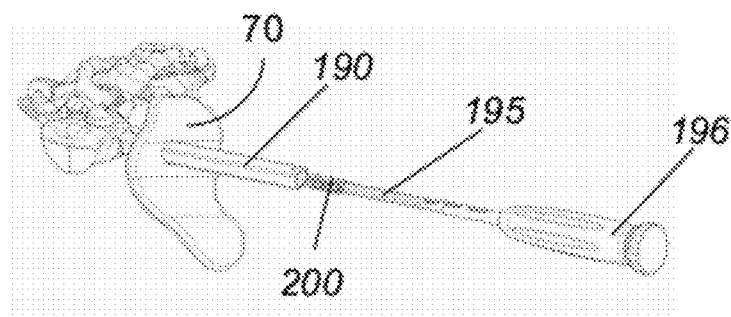
FIG. 24B depicts the step of inserting the intervertebral implant.
Figure 24C:
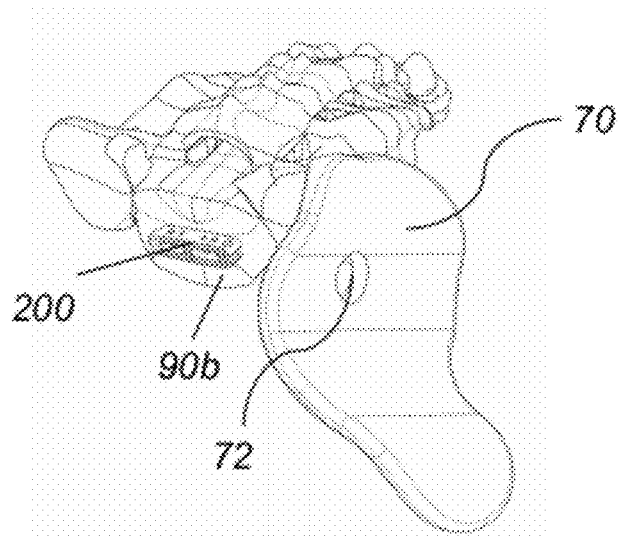
FIG. 24C depicts the inserted intervertebral implant.

Referring to FIG. 20A-24C, in another embodiment, a trans-iliac access is used for the placement of the intervertebral implant. First, a K-wire is inserted in the desired location and then with the guidance of anterior-posterior (AP) and lateral fluoroscopic imaging a lateral incision is made in the L5/S1 intervertebral joint 80 through the iliac crest 70 with a solid awl 270, shown in FIG. 20A. Next, a tissue protector 280 is slid over the solid awl 270 and is impacted into the iliac crest with inserter tool 230, shown in FIG. 20B. Next, the solid awl 270 is removed (shown in FIG. 20C), and a drill 285 is inserted into the tissue protector 280 and is used to drill an opening through the iliac crest 70, shown in FIG. 21A. Next, the nerve probe dilator 170 is inserted through the drilled opening and is advanced to the L5/S1 intervertebral joint 80, under fluoroscopic imaging and nerve monitoring with the nerve probe 175, shown in FIG. 21B. Next, the nerve probe dilator 170 is impacted into the L5/S1 intervertebral joint 80, shown in FIG. 21C. Next, the 18.4 mm trephine drill 180 is used to drill an access opening 72 through the iliac crest 70, shown in FIG. 22A and FIG. 22B. Next, the 8 mm, 10 mm and 12 mm stage dilators 120, 140 and 160, respectively, are used to created the desired space in the L5/S1 intervertebral joint 80 for the placement of the intervertebral implant 200, as shown in FIG. 22C-FIG. 23C, and described above. Next, a working cannula 190 is inserted over the largest dilation cannula and the working cannula is advanced to the desired L5/S1 intervertebral disc height, as shown in FIG. 24A. Next, all dilators are removed, and discectomy is performed using paddle shavers to rough up the endplates of the two adjacent vertebras, 90a, 90b. Finally, implant 200 is inserted with inserter 195 through cannula 190 and placed in the desired L5/S1 intervertebral space 80, as shown in FIG. 24B, and then the cannula 190 is removed, as shown in FIG. 24C.

Figure 26A:
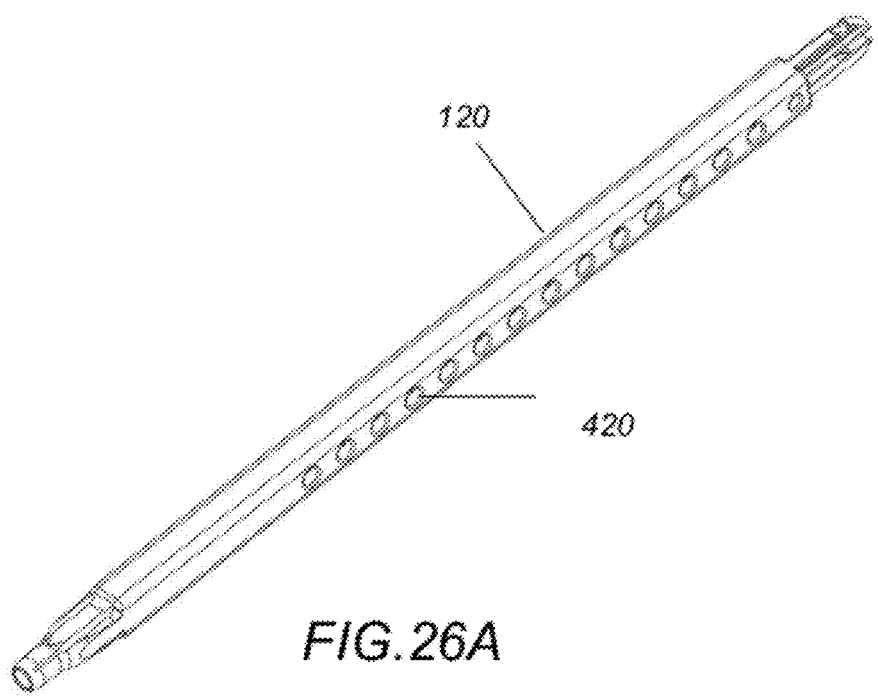
FIG. 26A depicts a perspective view of another embodiment of the 8 mm dilator.
Figure 26B:
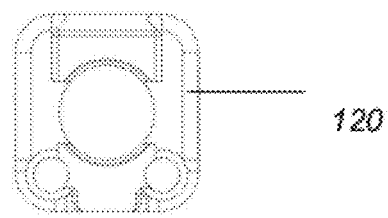
FIG. 26B is a bottom view of the 8 mm dilator of FIG. 26A.
Figure 26C:
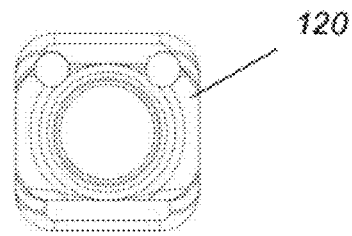
FIG. 26C is a top view of the 8 mm dilator of FIG. 26A.
Figure 31:
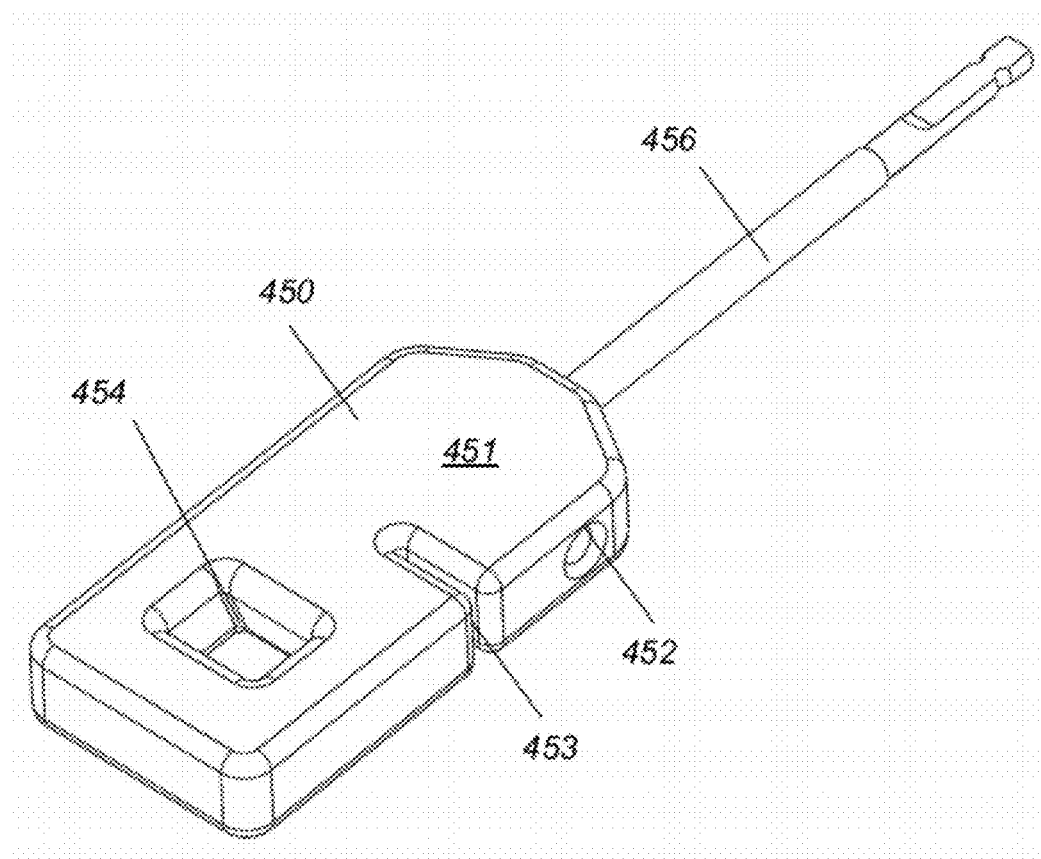
FIG. 31 depicts a multipurpose tool.
Figure 32A:
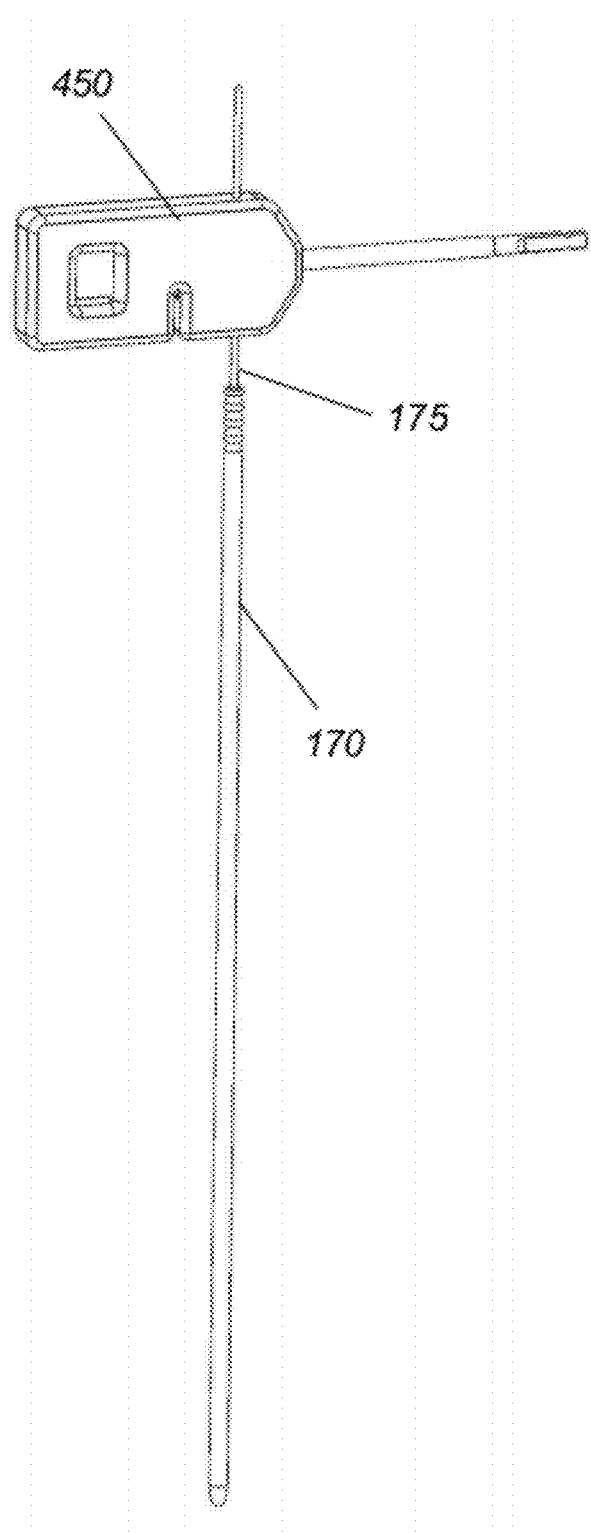
FIG. 32A depicts the multipurpose tool of FIG. 31 inserted over a nerve probe dilator.
Figure 32B:
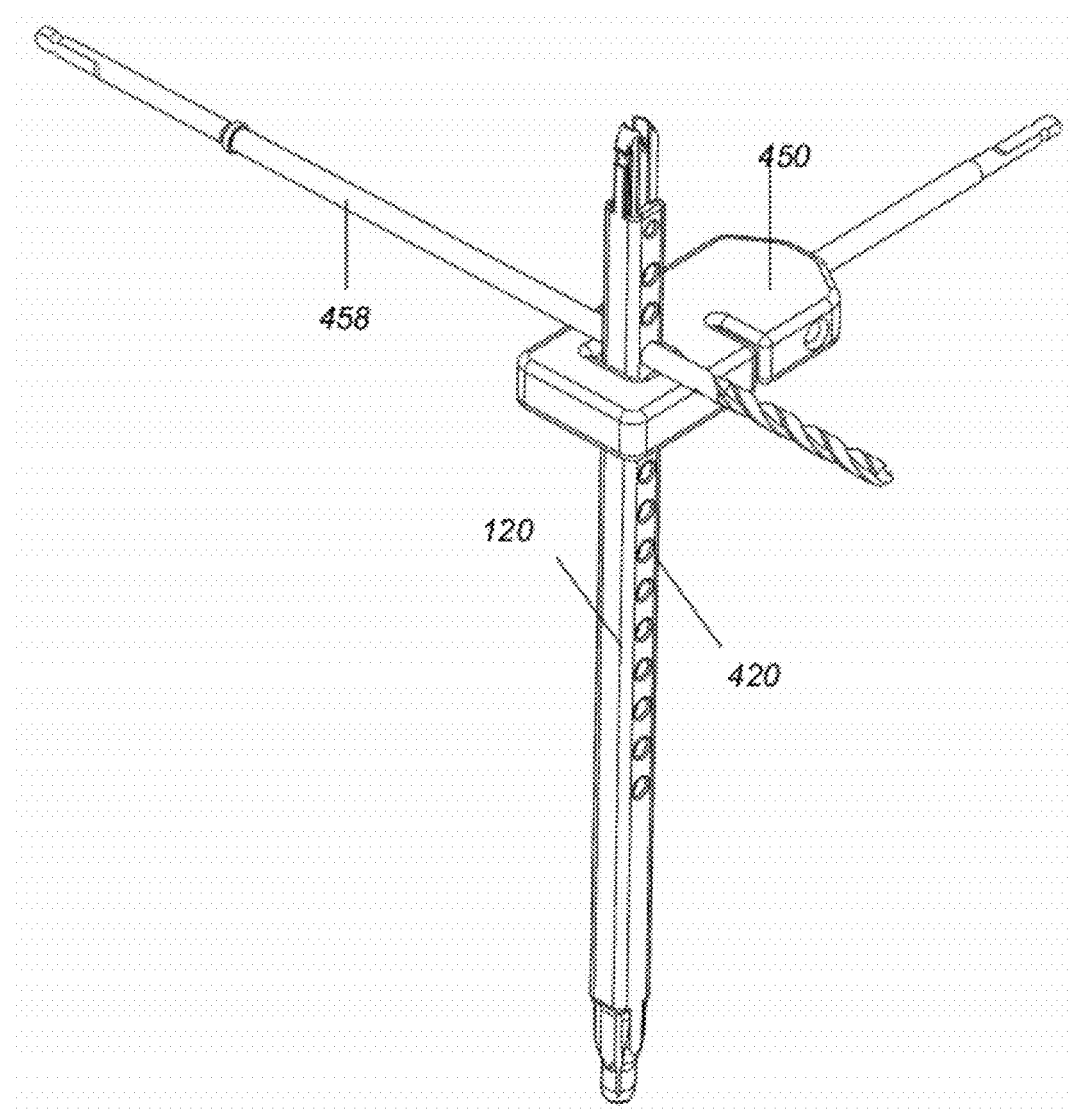
FIG. 32B depicts the multipurpose tool of FIG. 31 inserted over a cannula.

Access cannula system 100, 300 is made of metals, alloys, titanium, stainless steel, plastic or other inert materials. Typical dimensions include a length in the range of 100 mm to 250 mm, and cannula width or diameter in the range of 8 mm to 16 mm. In some embodiments, the 8 mm dilator 120 includes through-openings 420 extending perpendicular to the cylindrical inner lumen, as shown in FIG. 26A-FIG. 26C and in FIG. 29A-FIG. 29C and FIG. 30A-FIG. 30B. Through-openings 420 are used in connection with a multipurpose tool 450, as shown in FIG. 32B. Multipurpose tool 450 includes a plate-shaped body 451 having openings 454, 452, a side slot 453 and a rod 456 extending from a side surface, as shown in FIG. 31. Multipurpose tool 450 may be used as an impactor for the nerve probe dilator 170 as shown in FIG. 32A. In this configuration the nerve probe 175 is threaded through opening 452 and a force is applied onto the plate-shaped body 451 in order to impact the nerve probe 170 into a spinal location. Multipurpose tool 450 may also be used as an impactor for the 8 mm dilator 120, as shown in FIG. 32B. In this configuration, the 8 mm dilator is inserted into opening 454 and a crossbar 458 is inserted through one of the through-openings 420 in the 8 mm dilator above the plate-shaped body 451 in order to prevent the 8 mm dilator from sliding through the opening 454. The plate-shaped body 451 is oriented perpendicular to the main axis of the 8 mm dilator and a force is applied onto the plate-shaped body 451 in order to impact the dilator into a spinal location.

Other tools used in connection with the cannula system 100 include a pedicle reamer tool 460, shown in FIG. 33A and FIG. 33B, a nerve shield tool 470, shown in FIG. 34, a cannula holder 480, shown in FIG. 35A-FIG. 35B, and a tissue shim dilator 490, shown in FIG. 36A-FIG. 36D. The pedicle reamer tool 460 includes a cylindrical shaft 462, a reamer 464 at the distal end of the shaft 462 and a handle 466 at the proximal end of the shaft 462. The nerve shield 470 includes an elongated semi-cylindrical body 472 and a handle 474 that is oriented at an angle relative to the elongated semi-cylindrical body 472. The elongated semi-cylindrical body 472 is placed in front of the nerve that is intended to shield. The cannula holder tool 480 includes two spring loaded handles 482a, 482b that are pivotally connected at pivot point 485. The two handles 482a, 482b have proximal ends that are configured to compress two inner springs 484a, 484b, in order to open and close the distal ends 486a, 486b, respectively. The distal ends 486a, 486b have inner surfaces shaped and dimensioned to match the outer shape and dimensions of the outer cannula. The tissue shim dilator 490 is used for pushing tissue out of the cannula 190 and it includes an elongated blade 491 having an L-shaped plate 492 attached to its proximal end. The L-shaped plate 492 includes two legs 492a, 492b that are perpendicular to each other and a rectangular through-opening 492 formed in leg 492a. The L-shaped plate 492 is attached to the elongated blade 491 so that leg 492a is vertical to the elongated plate 491 and leg 492b is parallel to the elongated plate 491 and it forms a gap 493 with the elongated plate 491. The tissue shim dilator is shaped and dimensioned to fit within the outer cannula 190, as shown in FIG. 36A, and FIG. 36B. Gap 493 is dimensioned so that leg 492b slides over the outer surface of the outer cannula 190, while blade 491 slides into the central opening of the outer cannula 190. Leg 492a acts a stop for the tissue shim dilator 490 and allows the end 490a of the blade 491 to reach the top of the cutout 430 of the outer cannula 190, as shown in FIG. 36B.

Several embodiments of the present invention have been described. Nevertheless, it will be understood that various modifications may be made without departing from the spirit and scope of the invention. Accordingly, other embodiments are within the scope of the following claims.

What is claimed is:

1. A cannula assembly for providing percutaneous access in minimally invasive spinal surgeries, comprising:
   an outer cannula;
   a nerve probe dilator;
   a multistage dilator system comprising a first dilator, a second dilator, a third dilator and a fourth dilator;
   wherein the outer cannula and the dilators are slidable relative to each other and are arranged sequentially so that the fourth dilator surrounds the nerve probe dilator, the third dilator slides over a surface of the fourth dilator, the second dilator slides over a surface of the third dilator, the first dilator slides over a surface of the second dilator, and the outer cannula surrounds the first dilator; and
   wherein each of the first, second, and third dilators comprises a single elongated blade terminating into a tapered distal end and having a proximal end comprising two parallel extensions and a groove formed between the two parallel extensions; and
   wherein the nerve probe dilator comprises a cylindrical main shaft having a conical shaped distal end and a cylindrical lumen extending the entire length of the cylindrical main shaft and being dimensioned to receive a nerve probe.

2. The assembly of claim 1, wherein the outer cannula comprises an elongated tube having first and second opposite sides, third and fourth opposite sides and a rectangular cross section and wherein the first and second opposite sides comprise distal ends terminating in two parallel fork extensions, respectively.

3. The assembly of claim 2, wherein the parallel fork extensions are tapered and terminate into inverted trapezoids.

4. The assembly of claim 2, wherein the parallel fork extensions are rigid and are dimensioned to fit within an intervertebral space.

5. The assembly of claim 2, wherein the distal end of the third side is shorter than the distal end of the fourth side.

6. The assembly of claim 1, wherein the nerve probe dilator further comprises a trephine drill surrounding the conical distal end.

7. The assembly of claim 1, further comprising a nerve probe impactor comprising an elongated cylindrical body having an elongated slot extending along the length of the cylindrical body.

8. The assembly of claim 1, further comprising an impaction handle comprising a rectangular cross section and being dimensioned to slide over the outer cannula.

9. The assembly of claim 1, further comprising a multipurpose tool comprising a rectangular body having openings shaped and dimensioned to slide over the nerve probe dilator, the dilators and the outer cannula.

10. The assembly of claim 1, further comprising a pedicle reamer tool.

11. The assembly of claim 1, further comprising a nerve shield tool.

12. The assembly of claim 1, further comprising a cannula holder tool and wherein the cannula holder comprises two pivotally connected spring loaded handles and wherein the two handles comprise proximal ends configured to compress two inner springs, respectively, and distal ends having inner surfaces shaped and dimensioned to match the outer shape and dimensions of the outer cannula.

13. A cannula assembly for providing percutaneous access in minimally invasive spinal surgeries, comprising:
an outer cannula;
a nerve probe dilator;
a multistage dilator system comprising a first dilator, a second dilator, a third dilator and a fourth dilator;
wherein the outer cannula and the dilators are slidable relative to each other and are arranged sequentially so that the fourth dilator surrounds the nerve probe dilator, the third dilator slides over a surface of the fourth dilator, the second dilator slides over a surface of the third dilator, the first dilator slides over a surface of the second dilator, and the outer cannula surrounds the first dilator;
wherein each of the first, second, and third dilators comprises an inner surface having tongue protrusions and each of the second and third and fourth dilators comprises an outer surface having an elongated groove and wherein the tongue protrusions of the first dilator are configured to slide and engage the elongated groove of the second dilator, the tongue protrusions of the second dilator are configured to slide and engage the elongated groove of the third dilator, and the tongue protrusions of the third dilator are configured to slide and engage the elongated groove of the fourth dilator.

14. A cannula assembly for providing percutaneous access in minimally invasive spinal surgeries, comprising:
an outer cannula;
a nerve probe dilator;
a multistage dilator system comprising a first dilator, a second dilator, a third dilator and a fourth dilator;
wherein the outer cannula and the dilators are slidable relative to each other and are arranged sequentially so that the fourth dilator surrounds the nerve probe dilator, the third dilator slides over a surface of the fourth dilator, the second dilator slides over a surface of the third dilator, the first dilator slides over a surface of the second dilator, and the outer cannula surrounds the first dilator; and
wherein the fourth dilator comprises a cylindrical inner lumen, rectangular outer surfaces, a cylindrical distal end with a serrated edge and a proximal end having two elongated parallel extensions separated by a distance equal to the diameter of the cylindrical inner lumen.

15. A cannula assembly for providing percutaneous access in minimally invasive spinal surgeries, comprising:
an outer cannula;
a nerve probe dilator;
a multistage dilator system comprising a first dilator, a second dilator, a third dilator and a fourth dilator;
wherein the outer cannula and the dilators are slidable relative to each other and are arranged sequentially so that the fourth dilator surrounds the nerve probe dilator, the third dilator slides over a surface of the fourth dilator, the second dilator slides over a surface of the third dilator, the first dilator slides over a surface of the second dilator, and the outer cannula surrounds the first dilator; and
wherein each of the third and fourth dilators comprises two parallel blades extending from a common proximal end and having separated distal ends terminating in inverted trapezoids.

16. A cannula assembly for providing percutaneous access in minimally invasive spinal surgeries, comprising:
an outer cannula;
a nerve probe dilator;
a multistage dilator system comprising a first dilator, a second dilator, a third dilator and a fourth dilator;
wherein the outer cannula and the dilators are slidable relative to each other and are arranged sequentially so that the fourth dilator surrounds the nerve probe dilator, the third dilator slides over a surface of the fourth dilator, the second dilator slides over a surface of the third dilator, the first dilator slides over a surface of the second dilator, and the outer cannula surrounds the first dilator;
wherein the nerve probe dilator comprises a cylindrical main shaft having a conical shaped distal end and a cylindrical lumen extending the entire length of the cylindrical main shaft and being dimensioned to receive a nerve probe; and
wherein the cylindrical main shaft comprises a plurality of through openings extending perpendicular to the cylindrical lumen.

17. A cannula assembly for providing percutaneous access in minimally invasive spinal surgeries, comprising:
a multistage cannula system comprising a first cannula, a second cannula, a third cannula and a fourth cannula;
a multistage dilator system comprising a first dilator, a second dilator, a third dilator and a fourth dilator;
a nerve probe dilators; and
wherein the cannulae and the dilators are slidable relative to each other and are arranged sequentially so that the fourth dilator surrounds the nerve probe dilator, the fourth cannula surrounds the fourth dilator, the third dilator slides over a surface of the fourth cannula, the third cannula surrounds the third dilator, the second dilator slides over a surface of the third cannula, the second cannula surrounds the second dilator, the first dilator slides over a surface of the second cannula, and the first cannula surrounds the first dilator; and
wherein each of the first, second, and third dilators comprises a single elongated blade terminating into a tapered distal end and having a proximal end comprising two parallel extensions and a groove formed between the two parallel extensions.

18. A method for providing percutaneous access in minimally invasive spinal surgeries for inserting a spinal implant, comprising:
providing a cannula assembly comprising an outer cannula, a nerve probe dilator and a multistage dilator system comprising a first dilator, a second dilator, a third dilator and a fourth dilator and wherein the outer cannula and the dilators are slidable relative to each other and are arranged sequentially so that the fourth dilator surrounds the nerve probe dilator, the third dilator slides over a surface of the fourth dilator, the second dilator slides over a surface of the third dilator, the first dilator slides over a surface of the second dilator, and the outer cannula surrounds the first dilator;
inserting a nerve probe into the nerve probe dilator and impacting the nerve probe dilator into a first spinal location under the guidance of the nerve probe;

sliding the fourth dilator over the nerve probe dilator and impacting the fourth dilator into the first spinal location thereby forming an opening in the first spinal location;

measuring the opening's dimensions and if the spinal implant's dimensions are smaller than the opening's dimensions sliding the outer cannula over the fourth dilator and impacting the outer cannula into the first spinal location; and then removing the dilators and inserting the spinal implant into the opening.

19. The method of claim 18, wherein if the spinal implant's dimensions are larger that the opening's dimensions, further comprising sequentially impacting the third, second and first dilators into the first spinal location until the spinal implant's dimensions are smaller than the opening's dimensions.

* * * * *